United States Patent
Yamada et al.

(10) Patent No.: US 6,688,157 B2
(45) Date of Patent: Feb. 10, 2004

(54) GAS SENSOR HAVING PRE-STRESSED TERMINAL FOR CONTACT WITH INSERTED SENSOR ELEMENT

(75) Inventors: Hirokazu Yamada, Nagoya (JP); Hiroshi Sugino, Aichi-ken (JP); Masato Ozawa, Toyota (JP); Syuichi Nakano, Kariya (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/271,554

(22) Filed: Oct. 17, 2002

(65) Prior Publication Data
US 2003/0074950 A1 Apr. 24, 2003

Related U.S. Application Data

(62) Division of application No. 09/649,056, filed on Aug. 29, 2000, now Pat. No. 6,477,887.

(30) Foreign Application Priority Data

Aug. 30, 1999 (JP) .......................... 11-243549
Oct. 19, 1999 (JP) .......................... 11-296445
Jul. 27, 2000 (JP) .......................... 2000-227489
Aug. 3, 2000 (JP) .......................... 2000-235731

(51) Int. Cl.$^7$ ..................... G01N 27/403; G01N 27/407
(52) U.S. Cl. ..................... 73/23.2; 73/23.31; 73/31.05; 204/424; 204/426
(58) Field of Search ................. 73/23.2, 23.31, 73/31.05; 204/424, 426, 427, 428

(56) References Cited

U.S. PATENT DOCUMENTS

| 4,362,609 A | * 12/1982 | Sano et al. ................ 204/428 |
| 4,818,363 A | 4/1989 | Bayha et al. .............. 204/426 |
| 5,031,445 A | 7/1991 | Kato et al. |
| 5,246,562 A | 9/1993 | Weyl et al. ............... 204/424 |
| 5,556,526 A | 9/1996 | Fukaya et al. ............. 204/425 |
| 5,573,650 A | 11/1996 | Fukaya et al. ............. 204/424 |
| 5,830,339 A | 11/1998 | Watanabe et al. |
| 5,900,129 A | * 5/1999 | Tsuji et al. ............... 204/427 |
| 6,258,234 B1 | * 7/2001 | Watanabe et al. .......... 204/424 |

FOREIGN PATENT DOCUMENTS

| JP | 2-238355 | 9/1990 |
| JP | 4-110972 | 9/1992 |
| JP | 5-43411 | 11/1993 | ............... 73/23.31 |
| JP | 6-111872 | 4/1994 |
| JP | 6-222039 | 8/1994 | ............... 204/429 |
| JP | 9-127050 | 5/1997 |

* cited by examiner

Primary Examiner—Daniel S. Larkin
(74) Attorney, Agent, or Firm—Nixon & Vanderhye PC

(57) ABSTRACT

A gas sensor element is inserted into a housing having a base end and is fixed with respect to the housing. Terminal electrodes are provided on the base end of the sensor element. An atmosphere-side cover including an insulator with terminal accommodation holes is provided on the base end of the housing. The insulator also has an element accommodation hole (communicating with the terminal accommodation holes) in which the base end of the sensor element is placed. The insulator has ribs forming inner surfaces defining the element accommodation hole. The rib thickness is smaller than that of the sensor element base end. Metal terminals are at least partially placed in respective terminal accommodation holes and have connecting portions with leads for external electrical connection. The ribs are located between the metal terminals to form spaces between the metal terminals. As the sensor element base end is placed in the element accommodation hole, terminal electrodes on the base end come into contact with the metal terminals and thereby electrically connected with the leads.

14 Claims, 27 Drawing Sheets

FIG. 35
FIG. 36
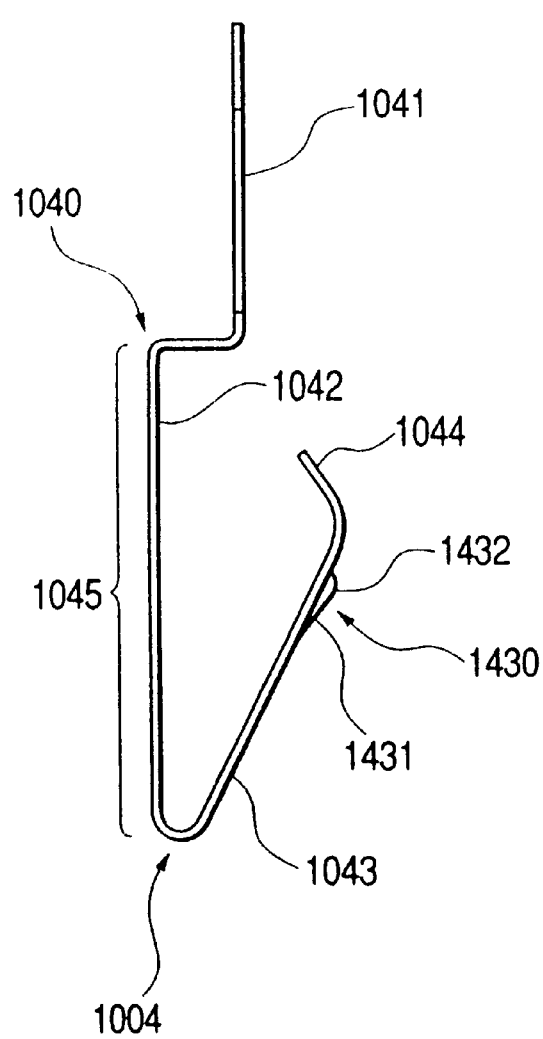
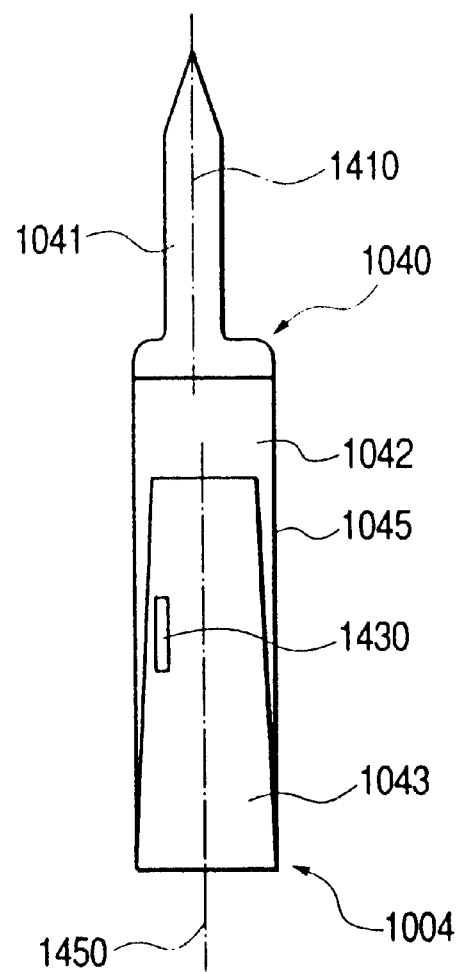

GAS SENSOR HAVING PRE-STRESSED TERMINAL FOR CONTACT WITH INSERTED SENSOR ELEMENT

RELATED APPLICATION

This is a division of our prior commonly assigned application Ser. No. 09/649,056 filed Aug. 29, 2000 now U.S. Pat. No. 6,477,887.

BACKGROUND OF THE INVENTION

1. Field of the Invention

This invention generally relates to a gas sensor. This invention relates to, for example, a gas sensor located in an exhaust system of an automotive internal combustion engine for measuring a specific-component concentration such as an oxygen concentration in an exhaust gas produced by the engine.

2. Description of the Related Art

FIG. 1 shows a prior-art gas sensor which includes a sensor element 920 inserted into a housing. An atmosphere-side cover is provided on the housing. An insulator 93 is provided in the housing. The insulator 93 has terminal accommodation holes 930 and 931. Two metal terminals 94 are placed in each of the terminal accommodation holes 930 and 931.

As shown in FIG. 2, each of the metal terminals 94 has a connecting portion 941 and a resilient contact portion 940. The resilient contact portion 940 is designed and formed as a leaf spring. The insulator 93 has ribs 91 providing insulation between the metal terminals 94 in the terminal accommodation hole 930 and the metal terminals 94 in the terminal accommodation hole 931.

A base end of the sensor element 920 is disposed in an element accommodation hole 92 formed among the metal terminals 94. As the sensor element 920 is placed in position, the sensor element 920 meets and then resiliently deforms the resilient contact portions 940 of the metal terminals 94. In this way, terminal electrodes of the sensor element 920 and the resilient contact portions 940 of the metal terminals 94 are brought into contact with each other. The deformation of the resilient contact portions 940 provides reliable electric contact between the metal terminals 94 and the terminal electrodes of the sensor element 920.

As the prior-art gas sensor in FIG. 1 is miniaturized, the size of the insulator 93 decreases and the element accommodation hole 92 among the metal terminals 94 narrows. In some cases, the metal terminals 94 are close to or in contact with each other before the sensor element 920 is placed in position.

With reference to FIG. 3, as the sensor element 920 is inserted into the insulator 93, the sensor element 920 meets the resilient contact portions 940 of the metal terminals 94. Then, the sensor element 920 is further pushed into the insulator 93 by a strong force, deforming and moving the resilient contact portions 940 of the metal terminals 94 away from each other along directions "a". Thus, a sufficient gap is formed between the resilient contact portions 940 of the metal terminals 94. The sensor element 920 moves through the region between the resilient contact portions 940 of the metal terminals 94 while sliding on and contacting with them.

The sensor element 920 is made of fragile material such as ceramic. Thus, the sensor element 920 tends to be damaged when being pushed against the resilient contact portions 940 of the metal terminals 94 by the strong force.

It is conceivable to thicken the sensor element 920 to increase its stiffness. Also, it is conceivable to increase the original distance between the metal terminals 94. In these cases, the body size of the prior-art gas sensor is large.

It is conceivable to reduce the spring performances of the resilient contact portions 940 of the metal terminals 94. In this case, the sensor element 920 can be placed in position with a weaker force. On the other hand, wrong electric contact tends to occur between the sensor element 920 and the resilient contact portions 940 of the metal terminals 94.

Thus, it is difficult that the prior-art gas sensor in FIG. 1 is miniaturized while reliable electric contact is provided between the sensor element 920 and the metal terminals 94.

SUMMARY OF THE INVENTION

It is an object of this invention to provide a small-sized gas sensor in which reliable electric contact is provided between a sensor element and a metal terminal (or metal terminals).

A first aspect of this invention provides a gas sensor comprising a housing having a base end; a sensor element inserted into the housing and fixed with respect to the housing, the sensor element having a base end; terminal electrodes provided on the base end of the sensor element; an atmosphere-side cover provided on the base end of the housing; an insulator provided in the atmosphere-side cover and having terminal accommodation holes, the insulator having an element accommodation hole in which the base end of the sensor element is placed, the element accommodation hole communicating with the terminal accommodation holes, the insulator having ribs forming inner surfaces defining the element accommodation hole, the ribs having a thickness smaller than a thickness of the base end of the sensor element; leads for electrical connection with an external; metal terminals at least partially placed in the terminal accommodation holes respectively and having connecting portions connected with the leads, the ribs being located between the metal terminals to form spaces between the metal terminals; wherein as the base end of the sensor element is placed in the element accommodation hole, the terminal electrodes on the base end of the sensor element come into contact with the metal terminals so that the terminal electrodes are electrically connected with the leads via the metal terminals.

A second aspect of this invention is based on the first aspect thereof, and provides a gas sensor wherein the metal terminals include the connecting portions connected with the leads, and resilient contact portions which are resiliently deformable, the resilient contact portions being in contact with the ribs while being resiliently deformed.

A third aspect of this invention is based on the first aspect thereof, and provides a gas sensor wherein the metal terminals have projections in contact with the terminal electrodes on the base end of the sensor element.

A fourth aspect of this invention is based on the first aspect thereof, and provides a gas sensor wherein the ribs include ribs for locating the metal terminals, and ribs for providing insulation between the metal terminals.

A fifth aspect of this invention is based on the second aspect thereof, and provides a gas sensor wherein the metal terminals have shoulders between the connecting portions and the resilient contact portions, the shoulders including bends at right angles.

A sixth aspect of this invention is based on the second aspect thereof, and provides a gas sensor wherein in each of the metal terminals, a central line of the connecting portion and a central line of the resilient contact portion are out of alignment.

A seventh aspect of this invention is based on the first aspect thereof, and provides a gas sensor wherein the base end of the sensor element has a taper portion.

An eighth aspect of this invention is based on the first aspect thereof, and provides a gas sensor wherein the ribs extend between the terminal accommodation holes.

A ninth aspect of this invention is based on the first aspect thereof, and provides a gas sensor wherein the insulator is fixed with respect to the atmosphere-side cover.

A tenth aspect of this invention provides a gas sensor comprising a housing having a base end; a sensor element inserted into the housing and fixed with respect to the housing, the sensor element having a base end; at least one terminal electrode provided on the base end of the sensor element; an atmosphere-side cover provided on the base end of the housing and having a base end and a front end; a resilient insulating member provided on the base end of the atmosphere-side cover and having at least one first insertion hole; an insulator provided in the front end of the atmosphere-side cover and having at least one second insertion hole; a lead placed in the first insertion hole; and a metal terminal placed in the second insertion hole and having a connecting portion electrically connected with the lead and a resilient contact portion electrically connected with the terminal electrode on the base end of the sensor element; wherein the resilient insulating member includes a first guide portion defining a front end of the first insertion hole and restricting motion of the lead, and the insulator includes a second guide portion defining a base end of the second insertion hole and restricting motion of the metal terminal.

An eleventh aspect of this invention is based on the tenth aspect thereof, and provides a gas sensor wherein the metal terminal includes a leaf spring.

A twelfth aspect of this invention is based on the tenth aspect thereof, and provides a gas sensor wherein the second guide portion has a length in a range of 1 mm to 5 mm.

A thirteenth aspect of this invention is based on the tenth aspect thereof, and provides a gas sensor wherein there are provided a plurality of the second guide portions, and a distance between centers of the second guide portions is in a range of 3 mm to 6 mm.

A fourteenth aspect of this invention is based on the tenth aspect thereof, and provides a gas sensor wherein the first guide portion has a length in a range of 3 mm to 8 mm.

A fifteenth aspect of this invention is based on the tenth aspect thereof, and provides a gas sensor wherein the insulator has at least one rib adjacent to the second insertion hole, the rib having a thickness smaller than a thickness of the sensor element, the metal terminal being in contact with the rib while being contracted in a radial direction of the insulator, and wherein the base end of the sensor element is placed in an element accommodation space formed between the rib and the metal terminal.

A sixteenth aspect of this invention is based on the tenth aspect thereof, and provides a gas sensor wherein the metal terminal has a projection in contact with the terminal electrode on the base end of the sensor element.

A seventeenth aspect of this invention is based on the tenth aspect thereof, and provides a gas sensor wherein there are provided a plurality of the ribs and a plurality of the metal terminals, the ribs including ribs for locating the metal terminals and ribs for electrically insulating the metal terminals from each other.

An eighteenth aspect of this invention is based on the tenth aspect thereof, and provides a gas sensor wherein the metal terminal has a shoulder between the connecting portion and the resilient contact portion, the shoulder including a bend at right angles.

A nineteenth aspect of this invention is based on the tenth aspect thereof, and provides a gas sensor wherein a central line of the connecting portion of the metal terminal and a central line of the resilient contact portion thereof are out of alignment.

A twentieth aspect of this invention is based on the tenth aspect thereof, and provides a gas sensor further comprising a metal member electrically connecting the metal terminal and the lead.

A twenty-first aspect of this invention is based on the twentieth aspect thereof, and provides a gas sensor wherein the first guide portion restricts motion of the metal member.

A twenty-second aspect of this invention is based on the twentieth aspect thereof, and provides a gas sensor wherein the metal member is inserted into the first guide portion.

A twenty-third aspect of this invention is based on the tenth aspect thereof, and provides a gas sensor wherein the atmosphere-side cover contains an internal space located between the resilient insulating member and the insulator, and the atmosphere-side cover has a hole communicating with the internal space for introducing atmosphere into the internal space.

A twenty-fourth aspect of this invention is based on the tenth aspect thereof, and provides a gas sensor wherein the insulator has an atmosphere introduction passage.

BRIEF DESCRIPTION OF THE DRAWINGS

FIG. 35 is a side view of a metal terminal in FIG. 29.

FIG. 36 is a front view of the metal terminal in FIG. 35.

DESCRIPTION OF THE PREFERRED EMBODIMENTS

First Embodiment

Figure 4:
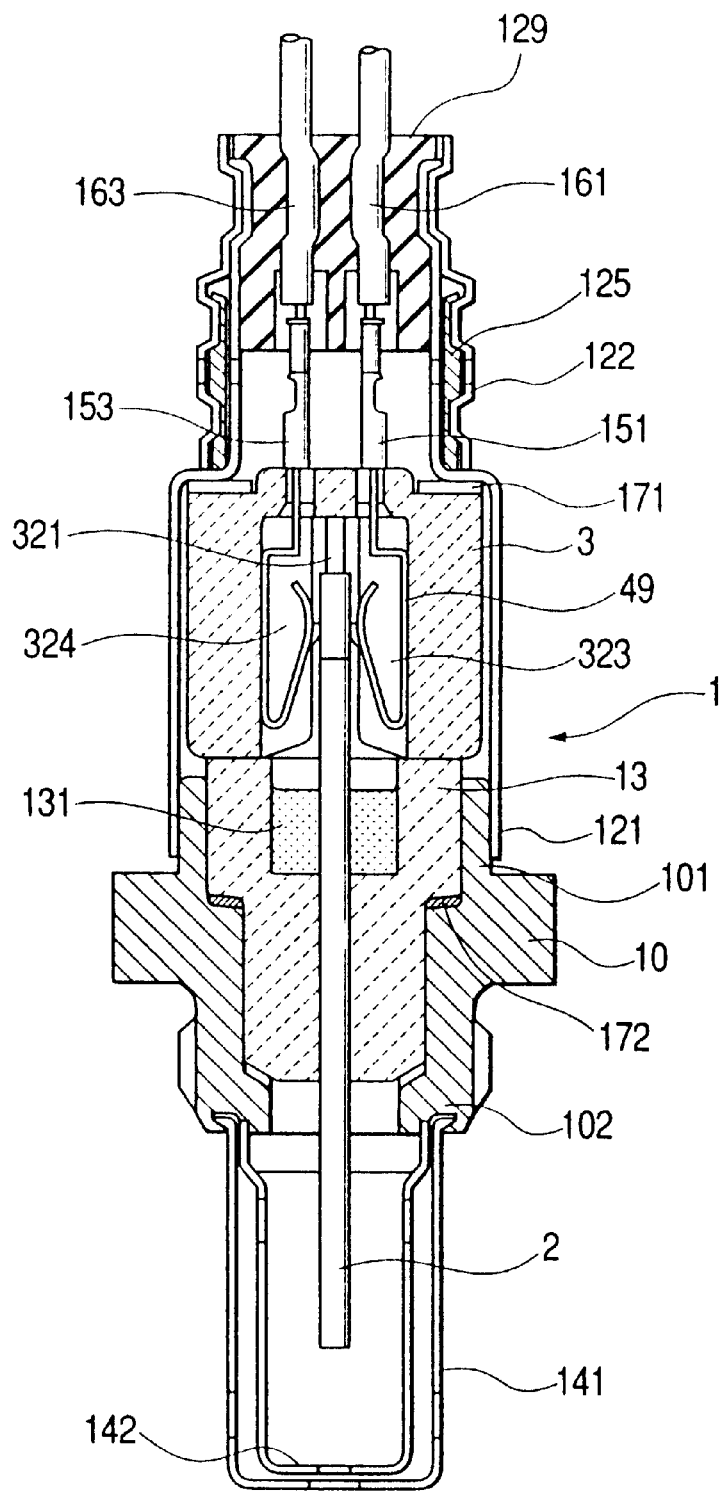
FIG. 4 is a sectional view of a gas sensor according to a first embodiment of this invention.

FIG. 4 shows a gas sensor 1 according to a first embodiment of this invention. The gas sensor 1 in FIG. 4 includes a sensor element 2, a housing 10, an atmosphere-side cover 121, and an insulator 3. The sensor element 2 is made of ceramic. The sensor element 2 is inserted into the housing 10. The sensor element 2 is fixed with respect to the housing 10. The housing 10 has a base end (an upper end) 101 on which the atmosphere-side cover 121 is provided. The insulator 3 is fixedly disposed in the atmosphere-side cover 121.

Figure 5:
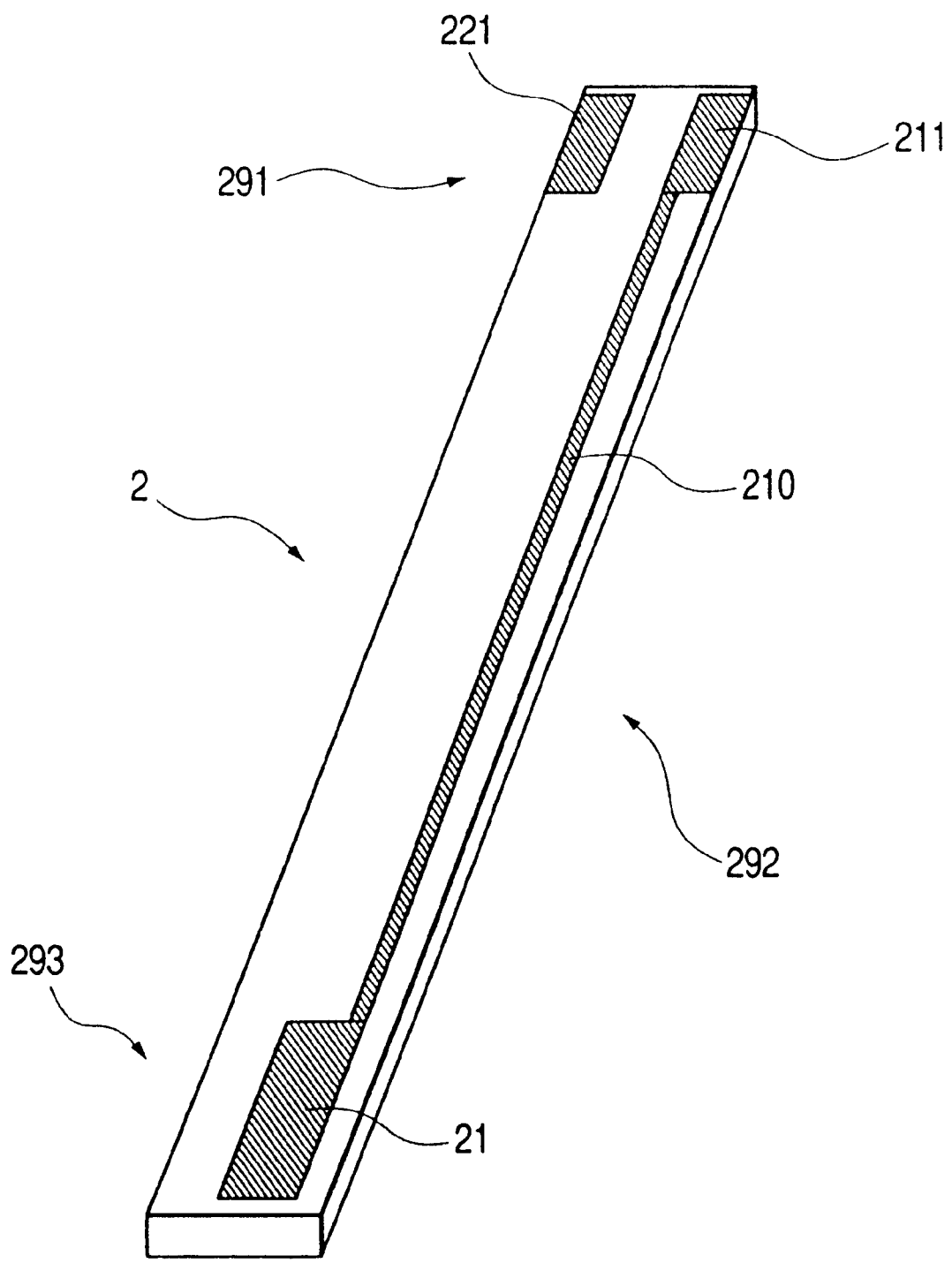
FIG. 5 is a perspective view of a sensor element in FIG. 4.

As shown in FIG. 5, the sensor element 2 has a base end 291 provided with four terminal electrodes including terminal electrodes 211 and 221. It should be noted that FIG. 5 indicates only two of the four terminal electrodes.

Figure 6:
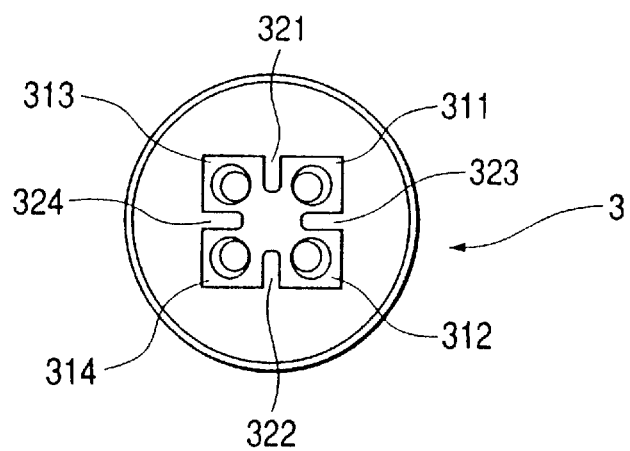
FIG. 6 is a plan view of a front end of an insulator in FIG. 4.
Figure 7:
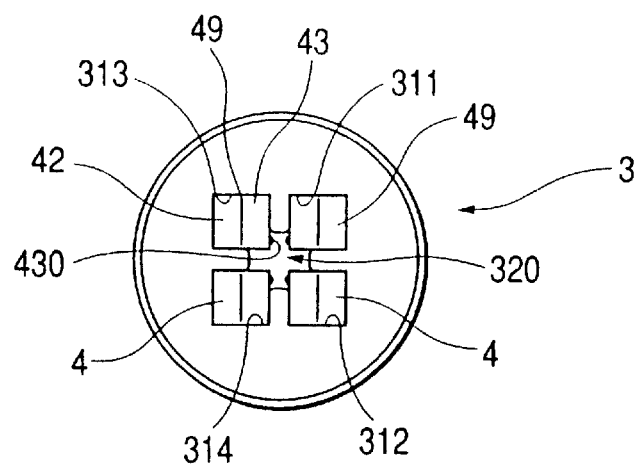
FIG. 7 is a plan view of metal terminals and the front end of the insulator in FIG. 4.

As shown in FIGS. 6 and 7, the insulator 3 has four terminal accommodation holes 311, 312, 313, and 314, and an element accommodation hole 320. The terminal accommodation holes 311–314 communicate with the element accommodation hole 320.

Figure 8:
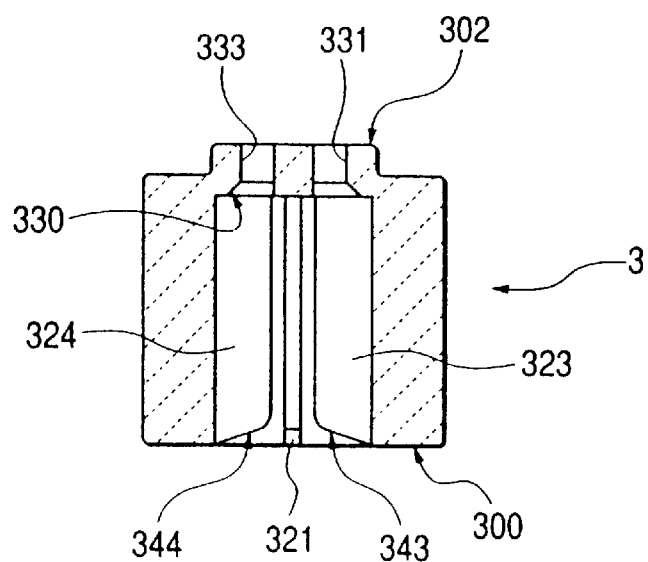
FIG. 8 is a sectional view of the insulator in FIG. 4.
Figure 9:
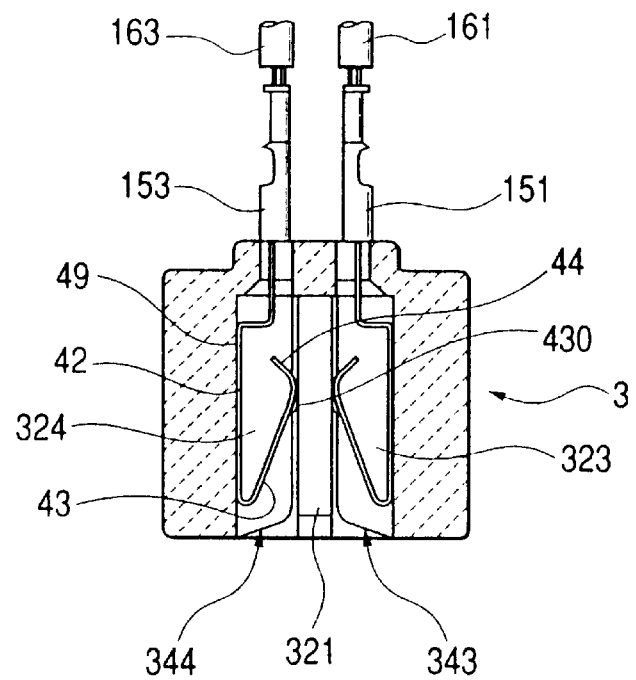
FIG. 9 is a sectional view of the metal terminals and the insulator in FIG. 4.

As shown in FIGS. 6, 8, and 9, the insulator 3 has ribs 321, 322, 323, and 324 which form inner surfaces defining the element accommodation hole 320. The ribs 323 and 324 are also referred to as the insulating ribs 323 and 324. The thickness of the ribs 321–324 is smaller than that of the sensor element 2. The sensor element 2 can be placed in the element accommodation hole 320.

Figure 10:
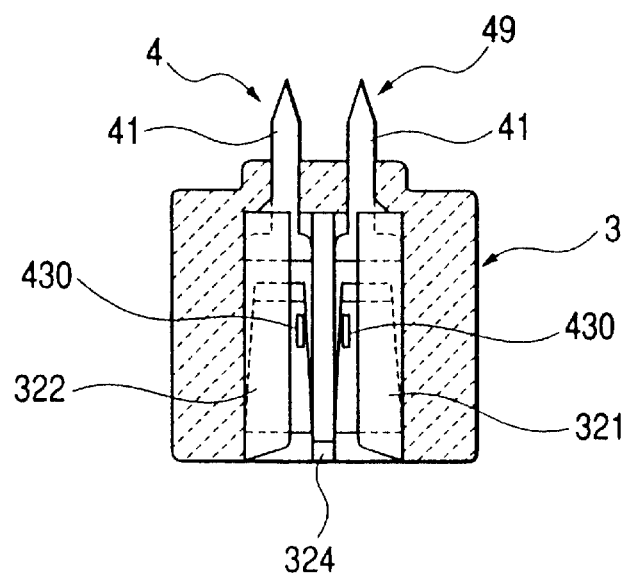
FIG. 10 is a sectional view of the metal terminals and the insulator in FIG. 4.
Figure 11:
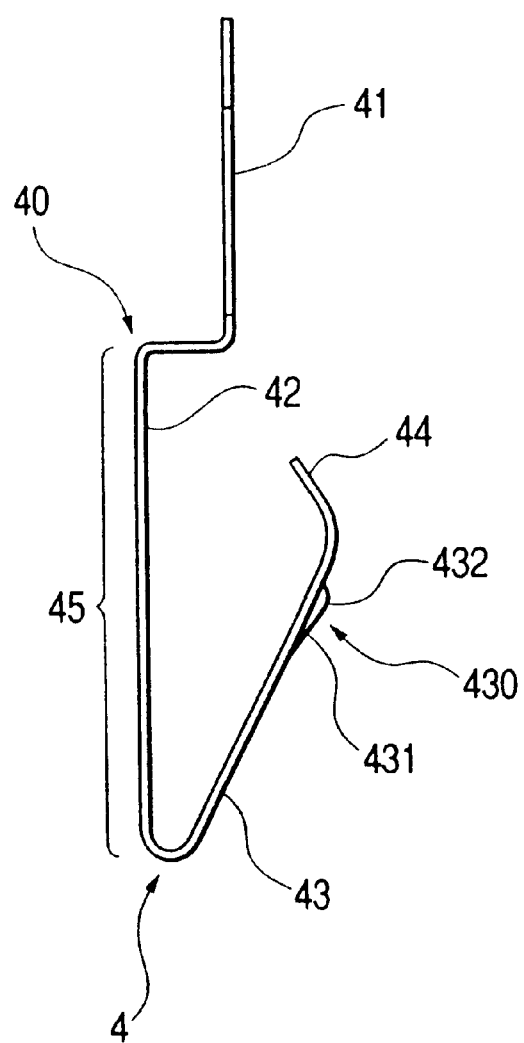
FIG. 11 is a side view of a metal terminal in FIG. 4.
Figure 12:
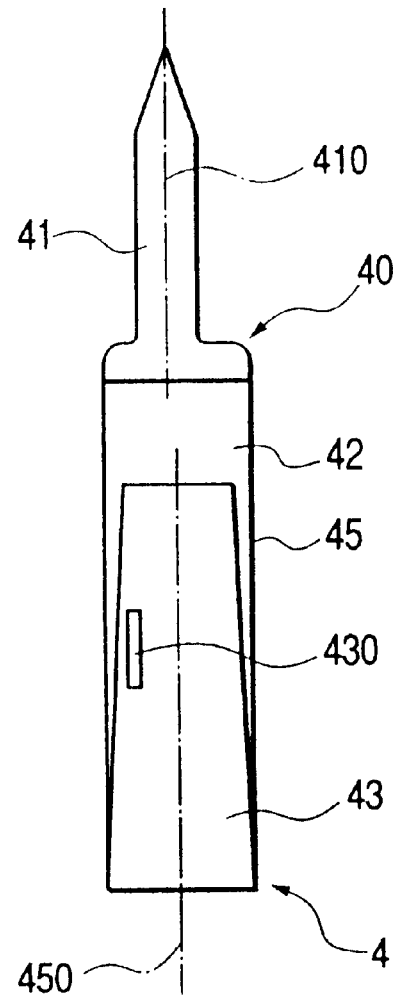
FIG. 12 is a front view of the metal terminal in FIG. 11.

As shown in FIGS. 7, 9, and 10, four metal terminals 4 and 49 are disposed in the terminal accommodation holes 311–314 respectively. A shape of the metal terminals 4 and a shape of the metal terminals 49 are in a left-right inverted relation. As shown in FIGS. 11 and 12, each of the metal terminals 4 has a connecting portion 41 and a resilient contact portion 45. The connecting portions 41 of the metal terminals 4 and 49 are connected with outer lead portions, that is, metal members including metal members 151 and 153 and leads including leads 161 and 163 which will be indicated later. In spaces surrounded by the ribs 321–324 and the inner surfaces defining the element accommodation hole 320, the resilient contact portions 45 of the metal terminals 4 and 49 are resiliently deformed by the ribs 321 and 322 while being in contact therewith.

When the base end 291 (see FIG. 5) of the sensor element 2 is placed in the element accommodation hole 320, the terminal electrodes 211 and 221 on the base end 291 of the sensor element 2 meet the corresponding metal electrodes 4 and 49 respectively. As a result, the terminal electrodes 211 and 221 are electrically connected with the outer lead portions via the metal terminals 4 and 49.

The gas sensor 1 in FIG. 4 will be described below in more detail. The gas sensor 1 includes the housing 10, the atmosphere-side cover 121, an atmosphere-side cover 122, and measurement-gas-side covers 141 and 142. The atmosphere-side cover 121 is provided on the base end (the upper end) 101 of the housing 10. The atmosphere-side cover 122 is provided on an upper portion of the atmosphere-side cover 121. The atmosphere-side cover 122 extends outward of the upper portion of the atmosphere-side cover 121. The housing 10 has a front end (a lower end) 102 on which the measurement-gas-side covers 141 and 142 are provided. The measurement-gas-side covers 141 and 142 compose a double-wall structure. The measurement-gas-side cover 142 extends inward of the measurement-gas-side cover 141.

The sensor element 2 is inserted into the housing 10. The sensor element 2 is fixed with respect to the housing 10. As shown in FIG. 5, the terminal electrodes 211 and 221 are provided on the base end 291 of the sensor element 2. The sensor element 2 has a front end (a lower end) 293 on which a measurement-gas-side electrode 21 is provided. The base end 291 of the sensor element 2 is located in the insulator 3 within the atmosphere-side cover 121. The front end (the lower end) 293 of the sensor element 2 is located in the measurement-gas-side cover 142.

As shown in FIG. 5, the measurement-gas-side electrode 21 is provided on the front end (the lower end) 293 of the sensor element 2. A reference electrode is provided on the sensor element 2. Specifically, the reference electrode faces an atmosphere chamber formed in the sensor element 2. A lead portion 210 formed on the sensor element 2 electrically connects the measurement-gas-side electrode 21 and the terminal electrode 211. Similarly, a lead portion formed on the sensor element 2 electrically connects the reference electrode and the terminal electrode 221. An output signal of the sensor element 2 which appears between the measurement-gas-side electrode 21 and the reference electrode can be transmitted to an external via the terminal electrodes 211 and 221.

With reference to FIG. 5, the two terminal electrodes 211 and 221 extend on the upper surface of the sensor element 2. Two terminal electrodes (not shown) extending on the lower surface of the sensor element 2 are electrically connected to a heater contained in the sensor element 2. Electric power can be fed to the heater via the terminal electrodes extending on the lower surface of the sensor element 2. The heater can be activated by the electric power.

As shown in FIG. 4, the atmosphere-side cover 121 is welded to the housing 10. The atmosphere-side cover 122 is fixed to the upper portion of the atmosphere-side cover 121 by pressing and deforming processes. A water repellent filter 125 is provided between the atmosphere-side covers 121 and 122.

A lower insulator 13 having a cylindrical shape is located in the housing 10. A central portion 292 (see FIG. 5) of the sensor element 2 extends through the lower insulator 13. The central portion 292 of the sensor element 2 is fixed to the lower insulator 13. Glass sealant 131 provides sealing between the lower insulator 13 and the central portion 292 of the sensor element 2.

As shown in FIG. 4, the insulator 3 is located in the atmosphere-side cover 121. The insulator 3 extends above the lower insulator 13. A rubber bush 129 is located in an upper end of the atmosphere-side cover 121. The rubber bush 129 extends above the insulator 3. The rubber bush 129 has four terminal accommodation holes into which four leads including leads 161 and 163 are inserted respectively. As shown in FIGS. 4, 7, and 9, these four leads are electrically connected to the four metal terminals 4 and 49 via the metal members (including the metal members 151 and 153), respectively.

As shown in FIGS. 6 and 7, the insulator 3 has the four terminal accommodation holes 311, 312, 313, and 314, and the element accommodation hole 320. The terminal accommodation holes 311–314 have approximately rectangular or square cross-sections. The element accommodation hole 320 axially extends through a central portion of the insulator 3. The terminal accommodation holes 311–314 extend outward of the element accommodation hole 320. The terminal accommodation holes 311–314 communicate with the element accommodation hole 320.

Figure 13:
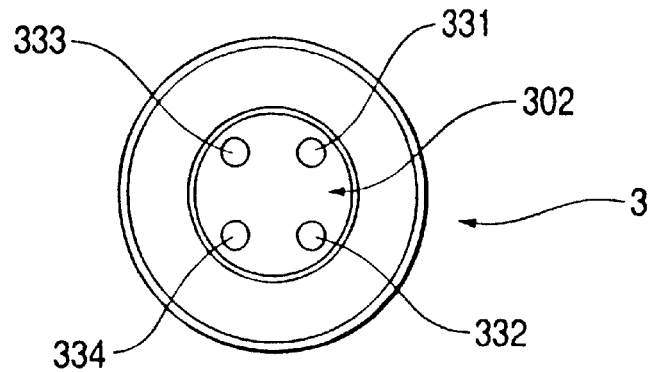
FIG. 13 is a plan view of a base end of the insulator in FIG. 4.

As shown in FIGS. 8 and 13, a base end (an upper end) 302 of the insulator 3 has four upper terminal accommodation holes 331, 332, 333, and 334 extending above and communicating with the terminal accommodation holes 311, 312, 313, and 314 respectively. The upper terminal accommodation holes 331–334 have circular cross-sections smaller than the cross-sections of the terminal accommodation holes 311–314. The insulator 3 is formed with taper portions 330 extending in the connection between the terminal accommodation holes 311–314 and the upper terminal accommodation holes 331–334.

As shown in FIGS. 6, 8, and 9, the insulator 3 has the ribs 321, 322, 323, and 324. The rib 321 extends between the terminal accommodation holes 311 and 313. The rib 322 extends between the terminal accommodation holes 312 and 314. The rib 323 extends between the terminal accommodation holes 311 and 312. The rib 324 extends between the terminal accommodation holes 313 and 314. The ribs 321–344 have bottom surfaces including bottom surfaces 343 and 344 located at a lower end 300 of the insulator 3. The bottom surfaces of the ribs 321–324 taper and extend along inclined directions from the central axis of the insulator 3 toward the outer circumference thereof.

As shown in FIGS. 11 and 12, each of the metal terminals 4 has a shoulder portion 40 in addition to the connecting portion 41 and the resilient contact portion 45. The shoulder portion 40 extends between the connecting portion 41 and the resilient contact portion 45. The shoulder portion 40 is formed by a bend at a right angle.

The resilient contact portion 45 has a back surface 42, an element contact surface 43, and a folded portion 44. The back surface 42 faces the walls of the insulator 3 which define the terminal accommodation hole 311, 312, 313, or 314. The element contact surface 43 faces the sensor element 2. The folded portion 44 extends toward the back surface 42.

A projection 430 is provided on the element contact surface 43. The projection 430 has slanting surfaces 431 and 432 located respectively at lower and upper sides as viewed in FIG. 11. The slope of the slanting surface 431 is gentler than the slope of the slanting surface 432.

As shown in FIG. 12, the central line 410 of the connecting portion 41 and the central line 450 of the resilient contact portion 45 are out of alignment by a distance in a left-right direction. Specifically, the central line 450 extends rightward of the central line 410. The projection 430 extends leftward of the central line 450 of the resilient contact portion 45.

As previously mentioned, the shape of the metal terminals 4 and the shape of the metal terminals 49 are in the left-right inverted relation. Therefore, in each of the metal terminals 49, the central line 450 of a resilient contact portion 45 extends leftward of the central line 410 of a connecting portion 41. In addition, in each of the metal terminals 49, a projection 430 extends rightward of the central line 450 of the resilient contact portion 45.

As best shown in FIG. 7, the metal terminal 49 is located in the terminal accommodation hole 311. The metal terminal 4 is located in the terminal accommodation hole 312. The metal terminal 49 is located in the terminal accommodation hole 313. The metal terminal 4 is located in the terminal accommodation hole 314.

Figure 14:
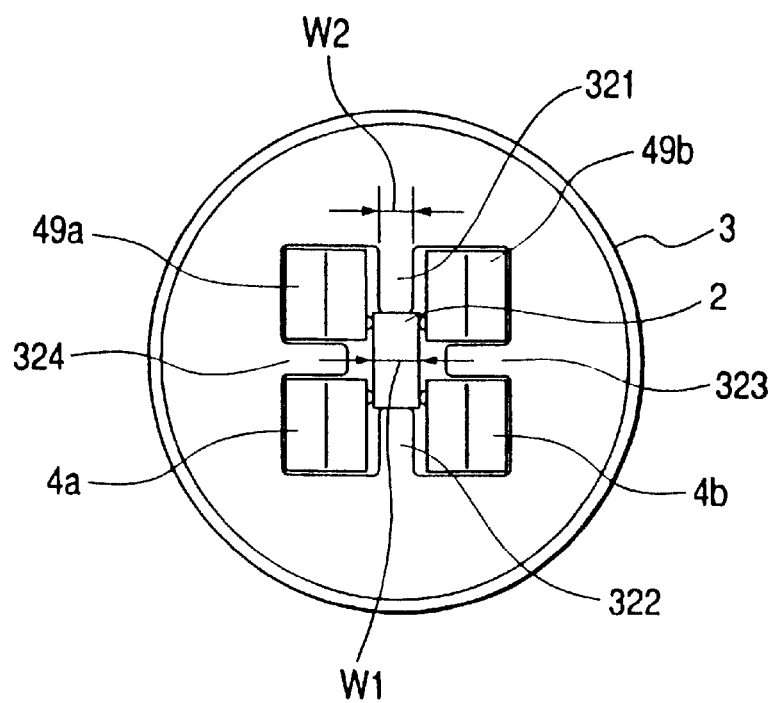
FIG. 14 is a plan view of the sensor element, the metal terminals, and the front end of the insulator in FIG. 4.

FIG. 14 shows a condition in which the sensor element 2 is inserted into the element accommodation hole 320 in the insulator 3. It should be noted that FIG. 14 uses characters "4a", "4b", "49a", and "49b" instead of the characters "4" and "49" to denote and identify the metal terminals. The metal terminals 4a and 49a contact the terminal electrodes 211 and 221 (see FIG. 5) on the sensor element 2. An output signal of the sensor element 2 is transmitted to an external via the metal terminals 4a and 49a. The metal terminals 4b and 49b contact the heater-power-feeding terminal electrodes on the sensor element 2. Electric power is fed from an external to the heater within the sensor element 2 via the metal terminals 4b and 49b.

Figure 15:
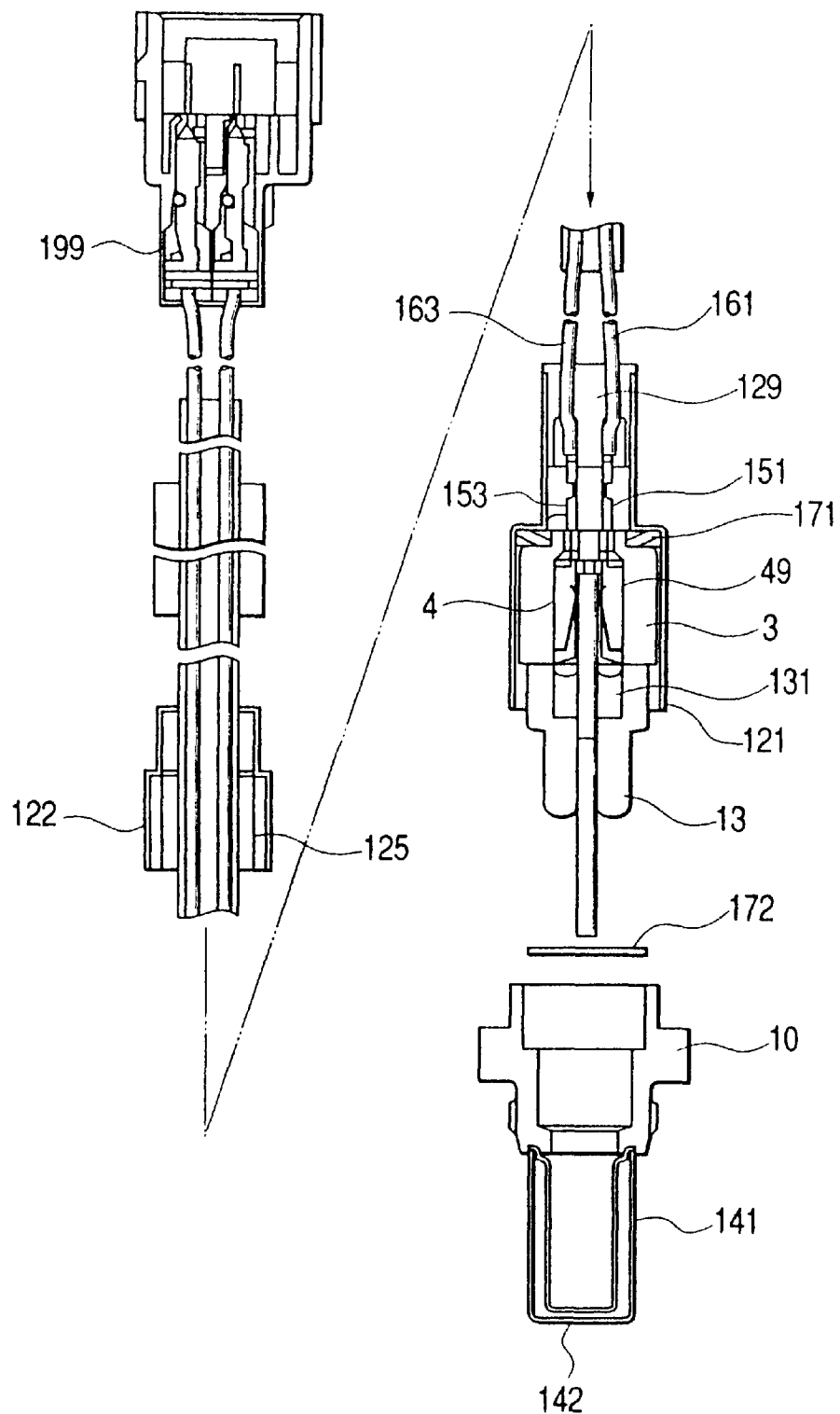
FIG. 15 is an exploded sectional view of the gas sensor in FIG. 4.

The gas sensor 1 in FIG. 4 is assembled as follows. With reference to FIG. 15, the measurement-gas-side covers 141 and 142 are fixed to the housing 10 by pressing and deforming processes. The housing 10 with the measurement-gas-side covers 141 and 142 is a housing assembly.

The sensor element 2 is passed through an axial center hole in the lower insulator 13. The sensor element 2 and the lower insulator 13 are bonded and fixed to each other by the glass sealant 131. The combination of the sensor element 2, the lower insulator 13, and the glass sealant 131 is an element assembly.

The leads including the leads 161 and 163 are inserted into the terminal accommodation holes in the rubber bush 129, respectively. The metal members including the metal members 151 and 153 are connected respectively to one ends of the leads including the leads 161 and 163 by pressing and deforming processes. The combination of the rubber bush 129, the leads, and the metal members is a wire assembly. The other ends of the leads are connected with a socket 199.

The metal terminals 4 and 49 are placed into the terminal accommodation holes 311–314, and the upper terminal accommodation holes 331–334 in the insulator 3, as shown in FIG. 13. The connecting portions 41 of the metal terminals 4 and 49 are fixed respectively to the metal members including the metal members 151 and 153 in the wire assembly by pressing and deforming processes. In addition, the connecting portions 41 are welded to the metal members.

Thereafter, a coned disc spring 171 is located near the base end (the upper end) of the insulator 3. In addition, the atmosphere-side cover 121 is placed in position. The bush 129 in the wire assembly is located in the atmosphere-side cover 121. Subsequently, the element assembly is inserted into the wire assembly, and is fixed thereto.

A ring-shaped floating packing 172 is placed in the housing 10 of the housing assembly. The element assembly which is combined with the wire assembly is inserted into the housing 10 of the housing assembly. An upper end of the housing 10 is fitted into a lower end of the atmosphere-side cover 121. The upper end of the housing 10 and the lower end of the atmosphere-side cover 121 are fixed to each other by a laser-based welding process implemented throughout the circumference. As a result, a main portion of the gas sensor 1 in FIG. 4 is completed.

In the gas sensor 1, the base end (the upper end) 291 of the sensor element 2 is located in the element accommodation hole 320 extending between the metal terminals 4 and 49 and the ribs 321 and 322. As shown in FIG. 14, the sensor element 2 has a predetermined thickness W1 greater than a thickness W2 of the ribs 321 and 322.

Figure 16:
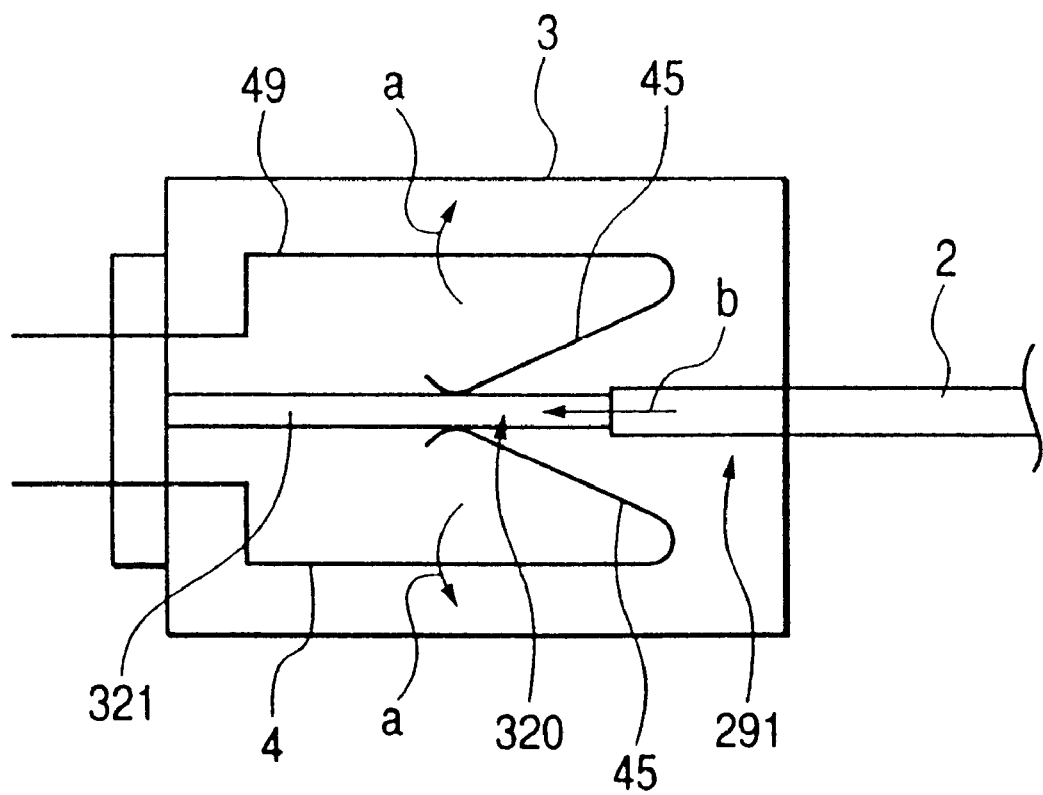
FIG. 16 is a diagram of a portion of the gas sensor in FIG. 4.

With reference to FIG. 16, before the sensor element 2 is placed in position, the resilient contact portions 45 of the metal terminals 4 and 49 are in contact with the ribs 321 and 322 while being resiliently deformed from their original shapes. Thus, even before the sensor element 2 is placed in position, a gap is formed between the resilient contact portions 45 of the metal terminals 4 and 49 by the ribs 321 and 322. As the sensor element 2 is inserted into the element accommodation hole 320 along a direction "b" (see FIG. 16), the sensor element 2 meets the resilient contact portions 45 of the metal terminals 4 and 49. Then, the sensor element 2 forces the resilient contact portions 45 away from each other along directions "a" (see FIG. 16), and expands the gap therebetween by only a small degree. Accordingly, the sensor element 2 receives only weak forces from the resilient contact portions 45 of the metal terminals 4 and 49. Thus, the sensor element 2 is prevented from being damaged. In addition, the sensor element 2 can easily be placed in position.

The thickness W2 of the ribs 321 and 322 is smaller than the thickness W1 of the sensor element 2. Therefore, before the sensor element 2 is placed in position, a thickness of the gap between the metal terminals 4 and 49 is smaller than the thickness W1 of the sensor element 2. Before the sensor element 2 is placed in position, the resilient contact portions 45 of the metal terminals 4 and 49 are in contact with the ribs 321 and 322. As the sensor element 2 is inserted into the element accommodation hole 320, the sensor element 2 meets the resilient contact portions 45 of the metal terminals 4 and 49. Then, the sensor element 2 forces the resilient contact portions 45 away from each other. In other words, the resilient contact portions 45 are resiliently deformed by the sensor element 2. The resilient deformations of the resilient contact portions 45 cause restoring forces which provide reliable mechanical and electrical contact between the sensor element 2 and the metal terminals 4 and 49.

Even before the sensor element 2 is placed in position, the ribs 321 and 322 form the gap between the resilient contact portions 45 of the metal terminals 4 and 49. Accordingly, it is unnecessary to make the insulator 3 large in size to allow a sufficient increase in the distance between the metal terminals 4 and 49. Thus, the insulator 3 can be small in size. Therefore, the gas sensor 1 can easily be miniaturized.

Before the sensor element 2 is placed in position, the resilient contact portions 45 of the metal terminals 4 and 49 are in contact with the ribs 321 and 322 while being resiliently deformed from their original shapes. Accordingly, the effective width of the metal terminals 4 and 49, which occur when they are inserted into the terminal accommodation holes 311–314, can be smaller. Thus, even in the case where the terminal accommodation holes 311–314 are narrow, it is possible to surely form the element accommodation hole 320 between the metal electrodes 4 and 49 and the ribs 321 and 322.

The metal terminals 4 and 49 have the resilient contact portions 45. During the insertion of the metal terminals 4 and 49 into the terminal accommodation holes 311–314, interference between the metal terminals 4 and 49 is prevented by using the resiliency of the resilient contact portions 45. Therefore, it is possible to easily place the metal terminals 4 and 49 in the terminal accommodation holes 311–314.

The projections 430 are provided on the resilient contact portions 45 of the metal terminals 4 and 49. The projections 430 provide more reliable electric contact between the metal terminals 4 and 49 and the terminal electrodes (including the terminal electrodes 211 and 221) on the sensor element 2. It should be noted that the projections 430 may be provided on the terminal electrodes of the sensor element 2 rather than the resilient contact portions 45 of the metal terminals 4 and 49.

As shown in FIG. 11, the projection 430 has the slanting surfaces 431 and 432. The slanting surface 431 faces a direction along which the sensor element 2 is moved during its placement in position. Thus, the sensor element 2 relatively slides on the slanting surface 431 during its placement in position. The slope of the slanting surface 431 is gentler than the slope of the slanting surface 432. Accordingly, it is possible to easily place the sensor element 2 in position.

The insulating rib 323 of the insulator 3 provides reliable insulation between the metal terminals 4 and 49. Also, the insulating rib 324 of the insulator 3 provides reliable insulation between the metal terminals 4 and 49.

Figure 1:
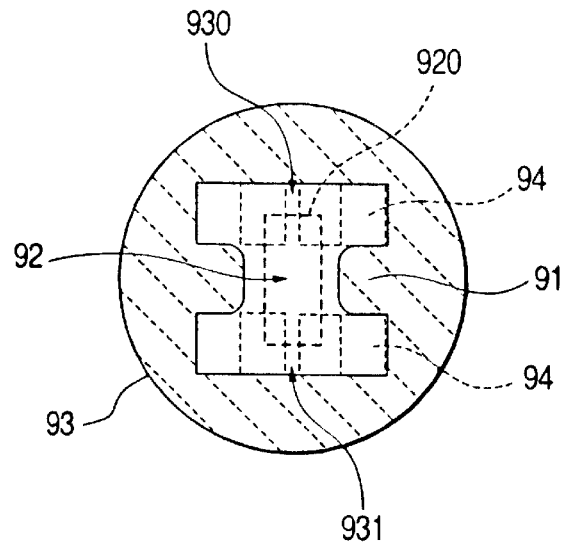
FIG. 1 is a plan view of a front end of an insulator in a prior-art gas sensor.
Figure 2:
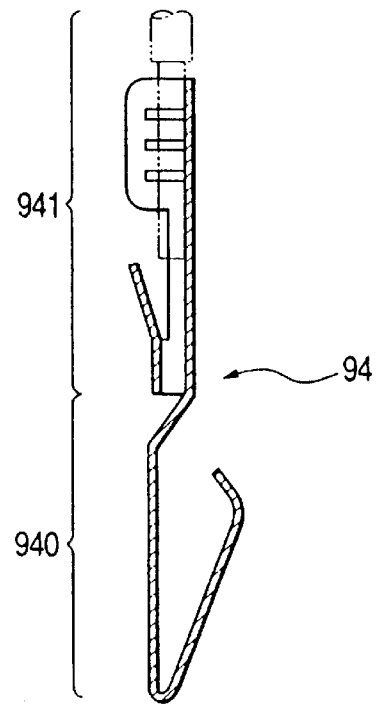
FIG. 2 is a sectional view of a metal terminal in FIG. 1.
Figure 3:
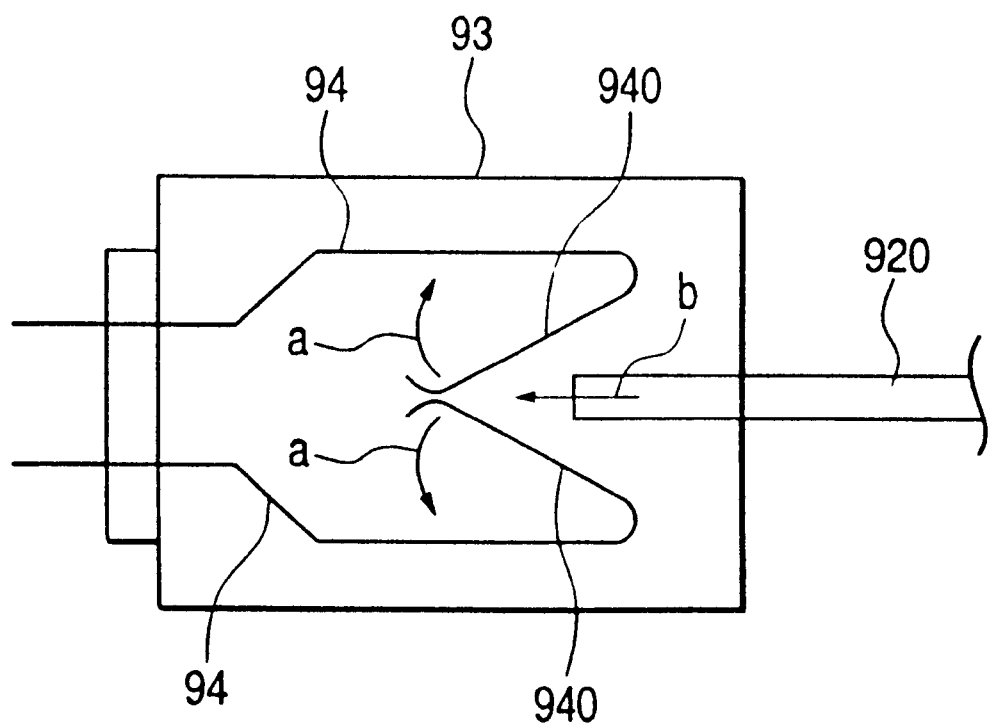
FIG. 3 is a diagram of a portion of the prior-art gas sensor in FIG. 1.

In each of the metal terminals 4 and 49, the shoulder 40 which extends between the connecting portion 41 and the resilient contact portion 45 is formed by a bend at a right angle. Thus, it is easy to carry the metal terminals 4 and 49. Each of the metal terminals 4 and 49 can be shorter than the prior-art metal terminal 94 in FIG. 2 which lacks a right-angled shoulder portion. Therefore, it is possible to miniaturize the gas sensor 1.

As shown in FIG. 12, the central line 410 of the connecting portion 41 and the central line 450 of the resilient contact portion 45 in each of the metal terminals 4 and 49 are out of alignment. Thus, as shown in FIG. 10, the connecting portions 41 of the metal terminals 4 and 49 can be closer to the central axis of the insulator 3. Accordingly, it is possible to miniaturize the insulator 3.

Second Embodiment

A second embodiment of this invention is similar to the first embodiment thereof except that a sensor element 2A replaces the sensor element 2.

Figure 17:
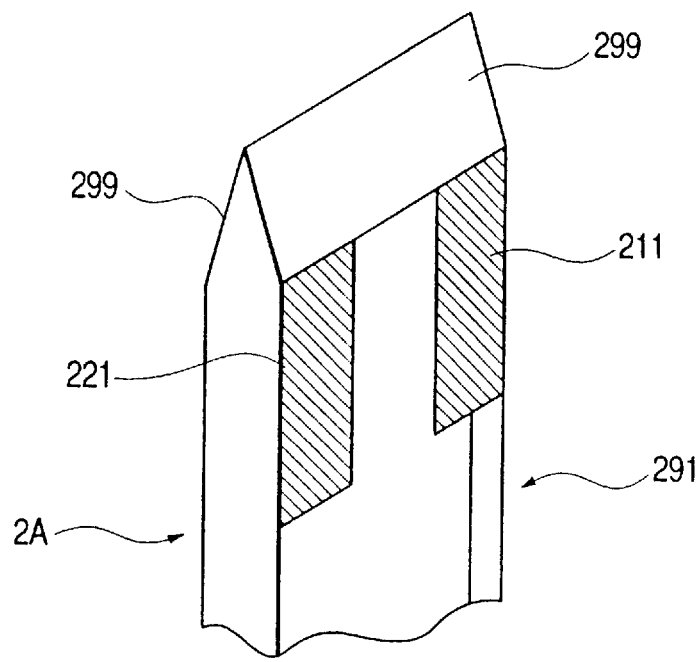
FIG. 17 is a perspective view of a base end, of a sensor element in a gas sensor according to a second embodiment of this invention.

As shown in FIG. 17, the sensor element 2A has a base end (an upper end) 291 formed with taper portions 299. The taper portions 299 enable the sensor element 2A to be smoothly placed into the element accommodation hole 320 (see FIG. 7).

Third Embodiment

A third embodiment of this invention is similar to the first embodiment thereof except that a sensor element 2B replaces the sensor element 2.

Figure 18:
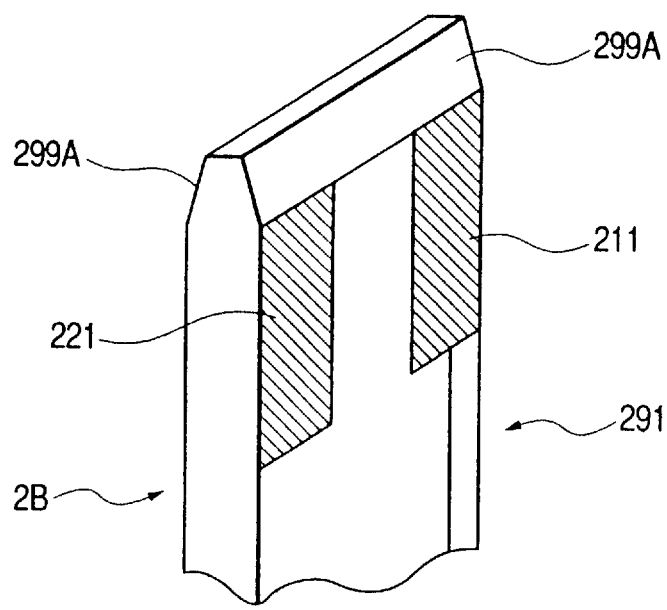
FIG. 18 is a perspective view of a base end of a sensor element in a gas sensor according to a third embodiment of this invention.

As shown in FIG. 18, the sensor element 2B has a base end (an upper end) 291 formed with taper portions 299A. The taper portions 299A enable the sensor element 2B to be smoothly placed into the element accommodation hole 320 (see FIG. 7).

Fourth Embodiment

A fourth embodiment of this invention is similar to the first embodiment thereof except for design changes mentioned later. The fourth embodiment of this invention includes an insulator 3C instead of the insulator 3. The fourth embodiment of this invention includes a sensor element 2C instead of the sensor element 2.

Figure 19:
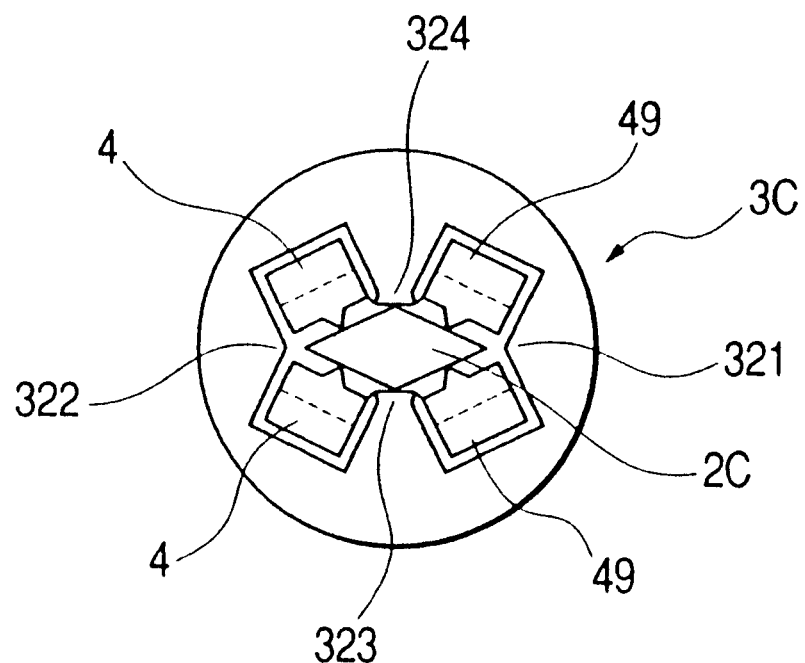
FIG. 19 is a plan view of a sensor element, metal terminals, and a front end of an insulator in a gas sensor according to a fourth embodiment of this invention.
Figure 20:
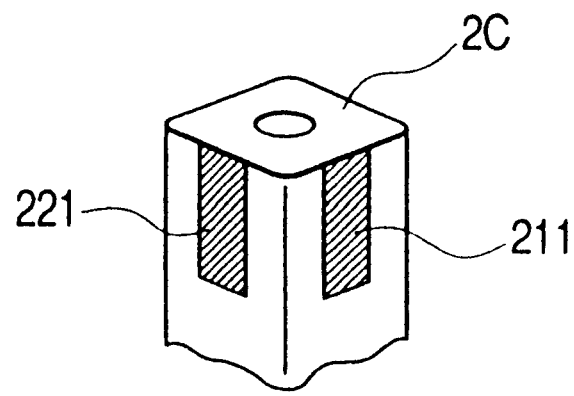
FIG. 20 is a perspective view of a base end of the sensor element in FIG. 19.

As shown in FIG. 19, ribs 321–324 of the insulator 3C have modified shapes. As shown in FIGS. 19 and 20, the sensor element 2C has a rhombic cross-section.

Fifth Embodiment

A fifth embodiment of this invention is similar to the first embodiment thereof except that an insulator 3D replaces the insulator 3.

Figure 21:
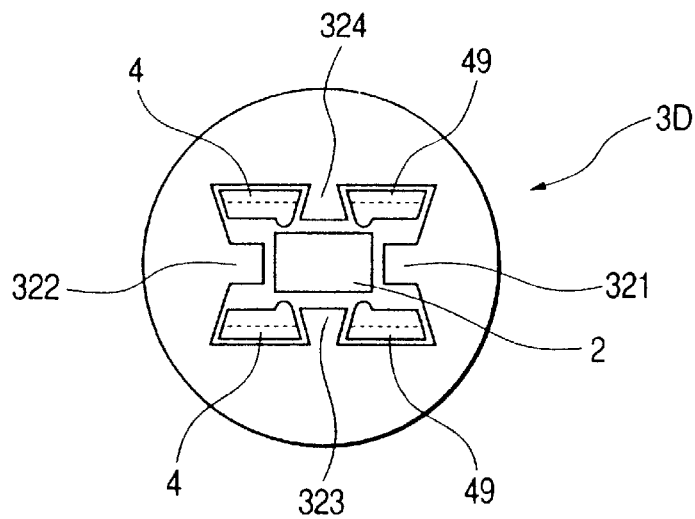
FIG. 21 is a plan view of a sensor element, metal terminals, and a front end of an insulator in a gas sensor according to a fifth embodiment of this invention.

As shown in FIG. 21, ribs 321–324 of the insulator 3D have modified shapes.

Sixth Embodiment

A sixth embodiment of this invention is similar to the first embodiment thereof except for design changes mentioned later. The sixth embodiment of this invention includes an insulator 3E instead of the insulator 3. The sixth embodiment of this invention includes a sensor element 2E instead of the sensor element 2.

Figure 22:
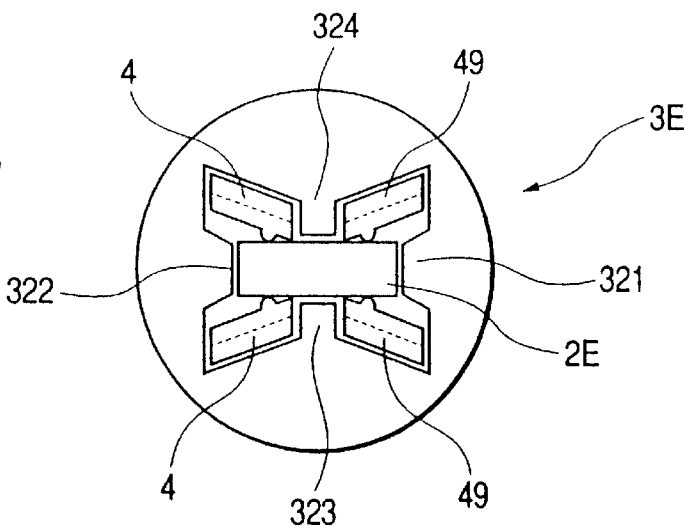
FIG. 22 is a plan view of a sensor element, metal terminals, and a front end of an insulator in a gas sensor according to a sixth embodiment of this invention.

As shown in FIG. 22, ribs 321–324 of the insulator 3E have modified shapes. The sensor element 2E has an elongated rectangular cross-section.

Seventh Embodiment

A seventh embodiment of this invention is similar to the first embodiment thereof except for design changes mentioned later. The seventh embodiment of this invention includes an insulator 3F instead of the insulator 3. The seventh embodiment of this invention includes a sensor element 2F instead of the sensor element 2.

Figure 23:
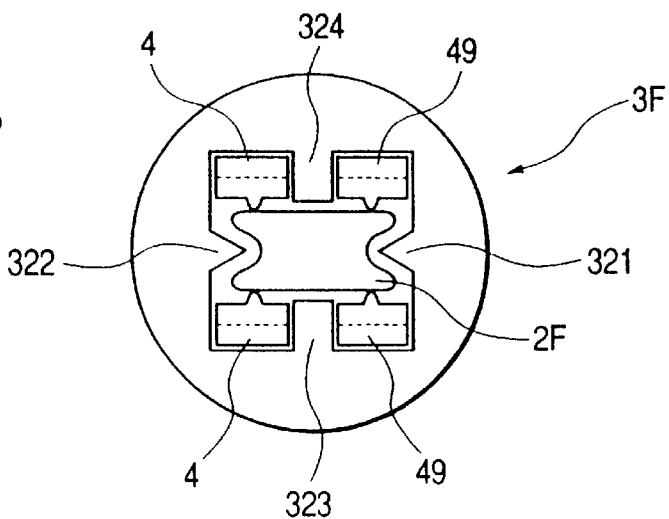
FIG. 23 is a plan view of a sensor element, metal terminals, and a front end of an insulator in a gas sensor according to a seventh embodiment of this invention.

As shown in FIG. 23, ribs 321–324 of the insulator 3F have modified shapes. The sensor element 2F has a cross-section with two recesses for accommodating the ribs 321 and 322 respectively.

Eighth Embodiment

An eighth embodiment of this invention is similar to the first embodiment thereof except for design changes mentioned later. The eighth embodiment of this invention includes an insulator 3G instead of the insulator 3. The eighth embodiment of this invention includes a sensor element 2G instead of the sensor element 2.

Figure 24:
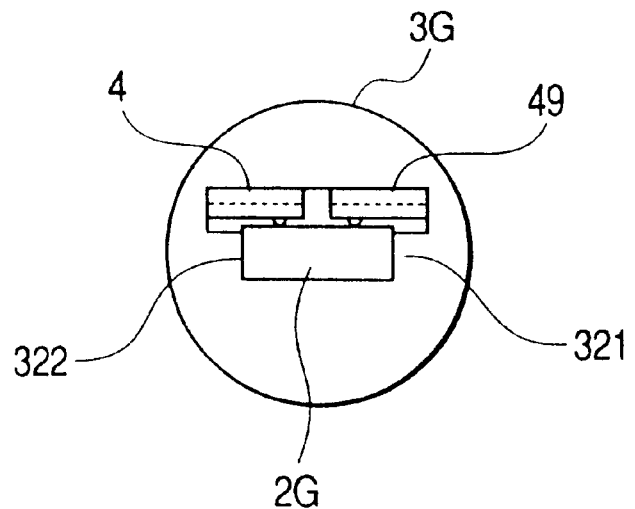
FIG. 24 is a plan view of a sensor element, metal terminals, and a front end of an insulator in a gas sensor according to an eighth embodiment of this invention.

As shown in FIG. 24, the insulator 3G has only two terminal accommodation holes arranged on a side-by-side basis. Metal terminals 4 and 49 are located in the terminal accommodation holes, respectively. The insulator 3G is formed with ribs 321 and 322 adjacent to the terminal accommodation holes. The insulator 3G has an element accommodation hole in communication with the terminal accommodation holes. The sensor element 2G which is placed in the element accommodation hole faces the metal terminals 4 and 49 in the terminal accommodation holes respectively.

It should be noted that the insulator 3G may be formed with a rib extending between the terminal accommodation holes.

Before the sensor element 2G is placed in position, resilient contact portions 45 of the metal terminals 4 and 49 are in contact with the ribs 321 and 322 while being resiliently deformed.

Ninth Embodiment

A ninth embodiment of this invention is similar to the first embodiment thereof except for design changes mentioned later. The ninth embodiment of this invention includes an insulator 3H instead of the insulator 3. The ninth embodiment of this invention includes a sensor element 2H instead of the sensor element 2.

Figure 25:
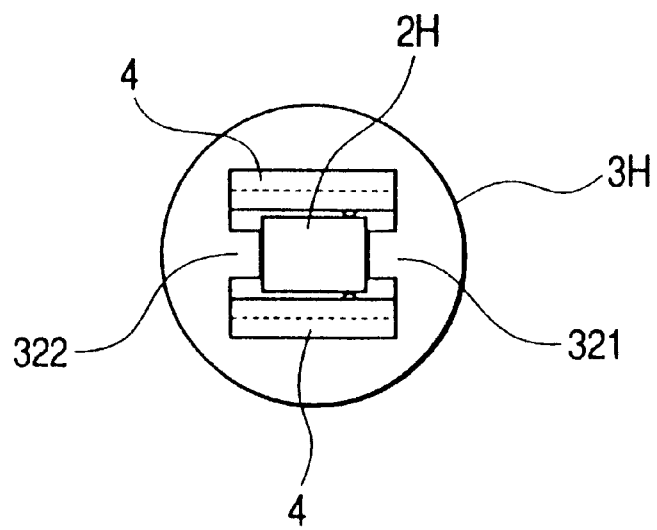
FIG. 25 is a plan view of a sensor element, metal terminals, and a front end of an insulator in a gas sensor according to a ninth embodiment of this invention.

As shown in FIG. 25, the insulator 3H has only two terminal accommodation holes. The terminal accommodation holes are at positions symmetrical with respect to the central axis of the insulator 3H. The terminal accommodation holes communicate with each other via an element accommodation hole. Metal terminals 4 are located in the terminal accommodation holes, respectively. The insulator 3H is formed with ribs 321 and 322 extending between the terminal accommodation holes. The sensor element 2H is placed between the metal terminals 4 in the terminal accommodation holes. The shapes of the metal terminals 4 are symmetrical with respect to the central axis of the insulator 3H. The shapes of the metal terminals 4 can be the same.

Before the sensor element 2H is placed in position, resilient contact portions 45 of the metal terminals 4 are in contact with the ribs 321 and 322 while being resiliently deformed.

Tenth Embodiment

Figure 26:
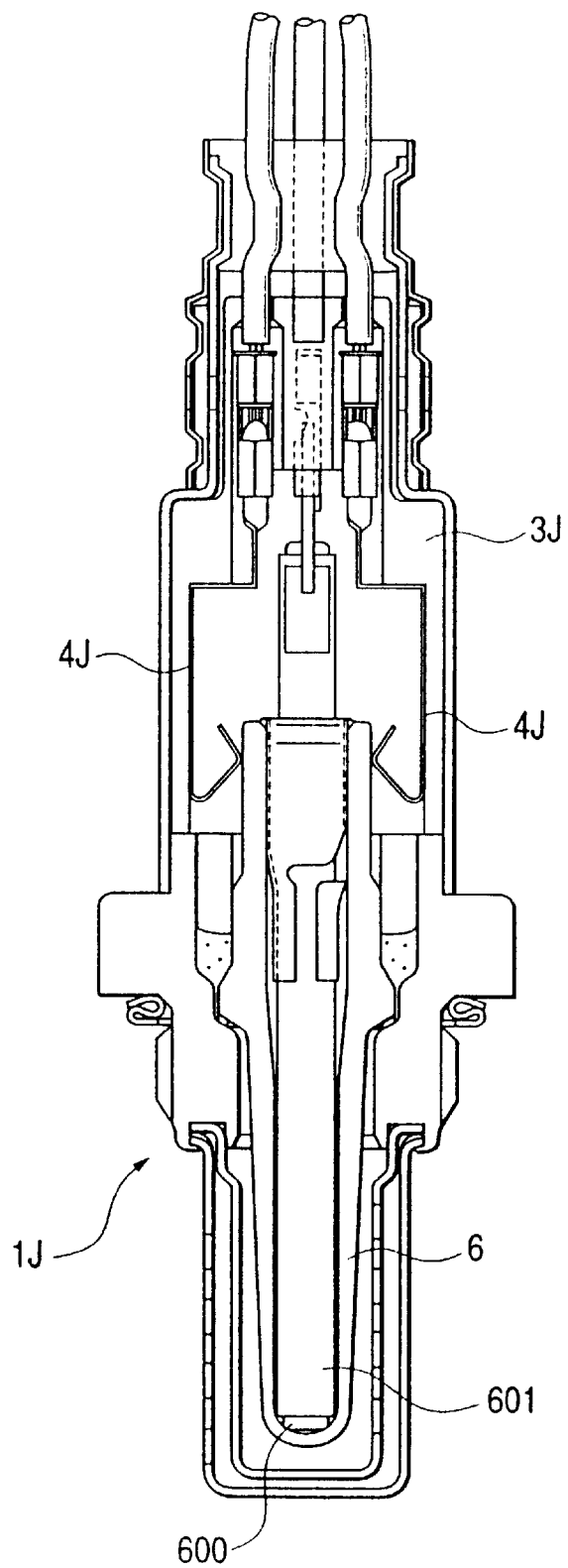
FIG. 26 is a sectional view of a gas sensor according to a tenth embodiment of this invention.

FIG. 26 shows a gas sensor 1J according to a tenth embodiment of this invention. The gas sensor 1J in FIG. 26 is similar to the gas sensor 1 in FIG. 4 except for design changes indicated below.

The gas sensor 1J in FIG. 26 includes a cup-shaped sensor element 6. An atmosphere chamber 600 is formed in the sensor element 6. The sensor element 6 includes a bar-like heater 601 inserted into the atmosphere chamber 600.

Figure 27:
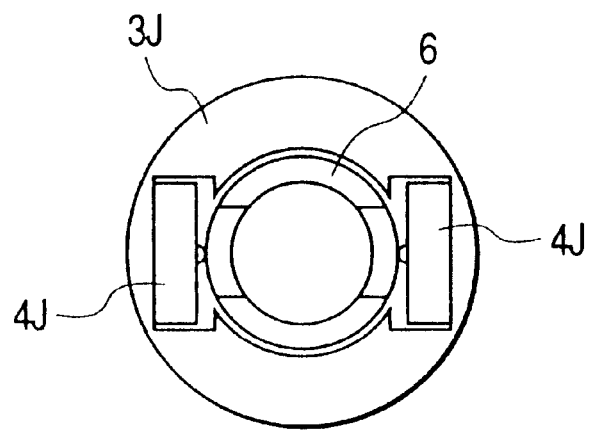
FIG. 27 is a plan view of a sensor element, metal terminals, and a front end of an insulator in FIG. 26.

The gas sensor 1J in FIG. 26 further includes an insulator 3J and metal terminals 4J. As shown in FIGS. 26 and 27, the insulator 3J has terminal accommodation holes in which the metal terminals 4J are located. Projections on resilient contact portions of the metal terminals 4J are in contact with terminal electrodes on the sensor element 6. It should be noted that projections may be provided on the terminal electrodes of the sensor element 6 rather than the resilient contact portions of the metal terminals 4J.

Figure 28:
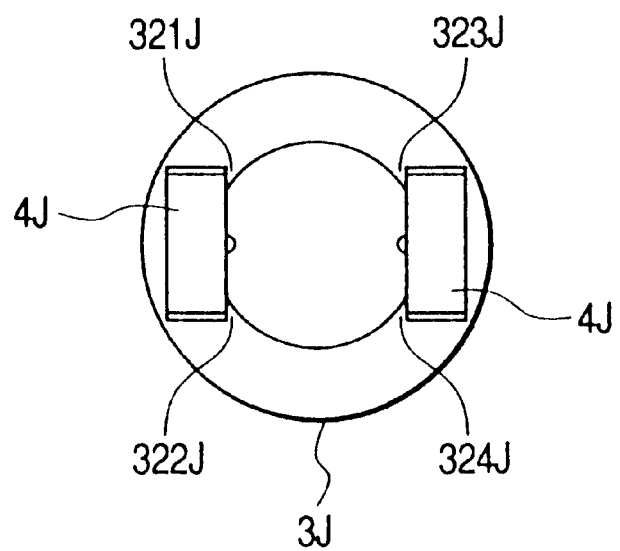
FIG. 28 is a plan view of the metal terminals and the front end of the insulator in FIG. 26.

With reference to FIG. 28, before the sensor element 6 is placed in position, resilient contact portions of the metal terminals 4J are in contact with ribs 321J–324J of the insulator 3J while being resiliently deformed from their original shapes. Thus, even before the sensor element 6 is placed in position, a gap is formed between the resilient contact portions of the metal terminals 4J by the ribs 321J–324J. As the sensor element 6 is inserted into the insulator 3J, the sensor element 6 meets the resilient contact portions of the metal terminals 4J. Then, the sensor element 6 forces the resilient contact portions away from each other, and expands the gap therebetween by only a small degree. Accordingly, the sensor element 6 receives only weak forces from the resilient contact portions of the metal terminals 4J. Thus, the sensor element 6 is prevented from being damaged. In addition, the sensor element 6 can easily be placed in position.

Eleventh Embodiment

Figure 29:
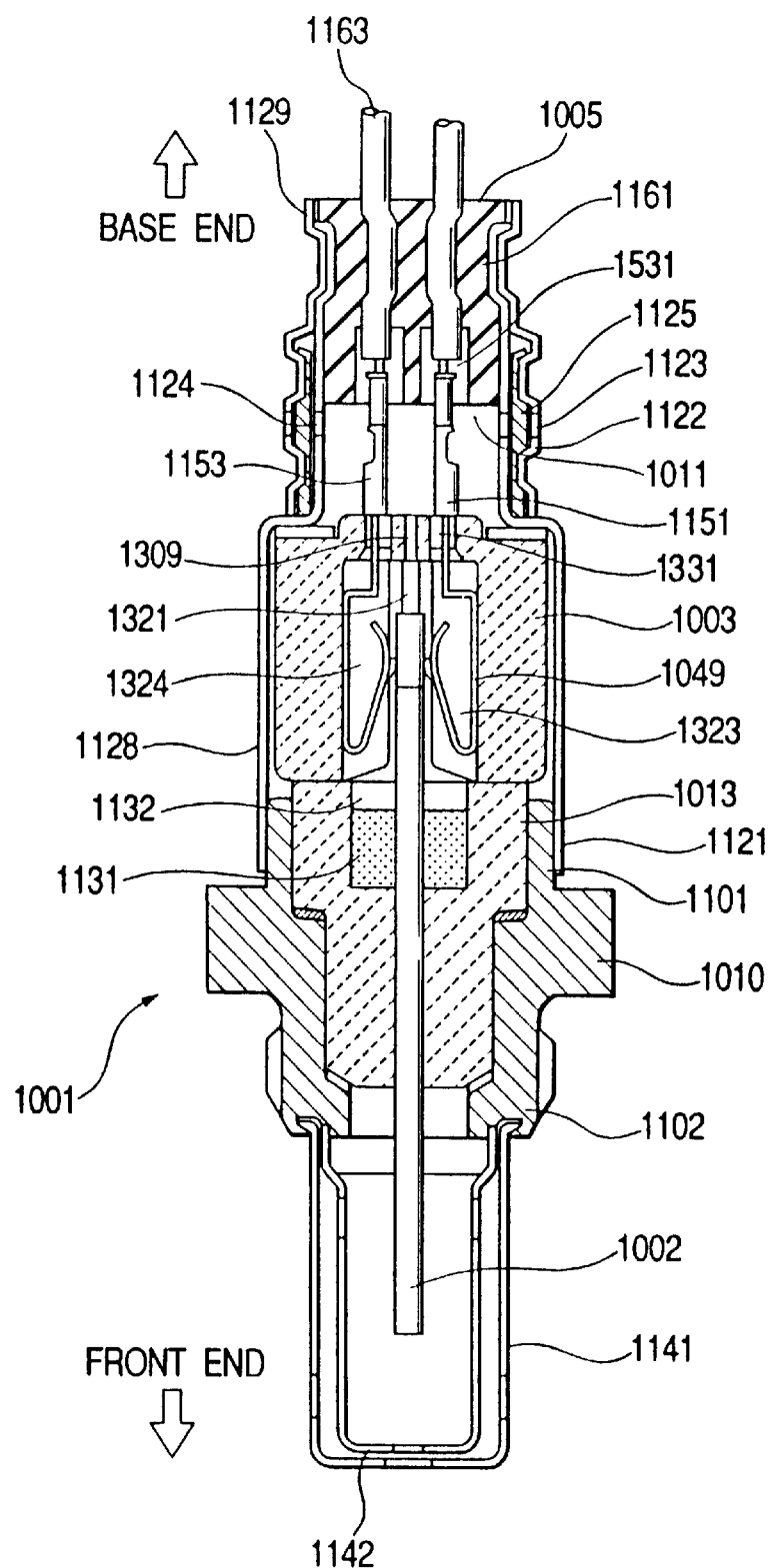
FIG. 29 is a sectional view of a gas sensor according to an eleventh embodiment of this invention.

FIG. 29 shows a gas sensor 1001 according to an eleventh embodiment of this invention. The gas sensor 1001 in FIG. 29 includes a sensor element 1002, a housing 1010, and atmosphere-side covers 1121 and 1122. The sensor element 1002 is inserted into the housing 1010. The sensor element 1002 is fixed with respect to the housing 1010. The housing 1010 has a base end (an upper end) 1101 on which the atmosphere-side cover 1121 is provided. The atmosphere-side cover 1122 fixedly extends around an upper portion of the atmosphere-side cover 1121.

The atmosphere-side covers 1121 and 1122 have holes 1123 and 1124 for introducing atmosphere. The holes 1123 and 1124 align in radial directions.

Figure 30:
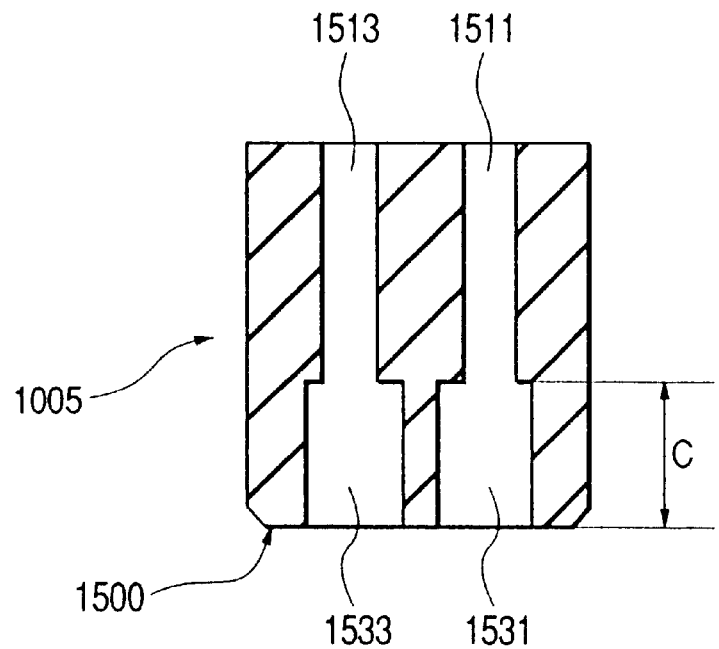
FIG. 30 is a sectional view of a resilient insulator in FIG. 29.
Figure 31:
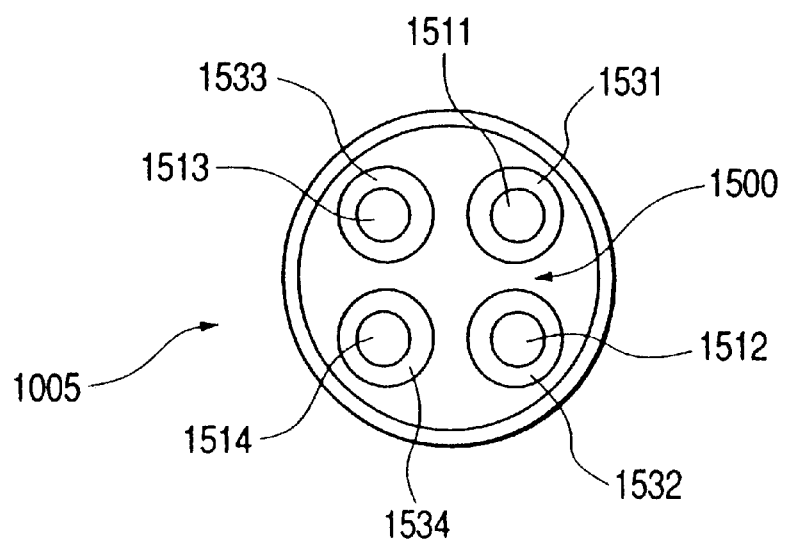
FIG. 31 is a plan view of a front end of the resilient insulator in FIG. 30.

A resilient insulator 1005 is fixedly disposed in a base end (an upper end) 1129 of the atmosphere-side cover 1121. As shown in FIGS. 30 and 31, the resilient insulator 1005 has four first insertion holes 1511, 1512, 1513, and 1514.

Figure 32:
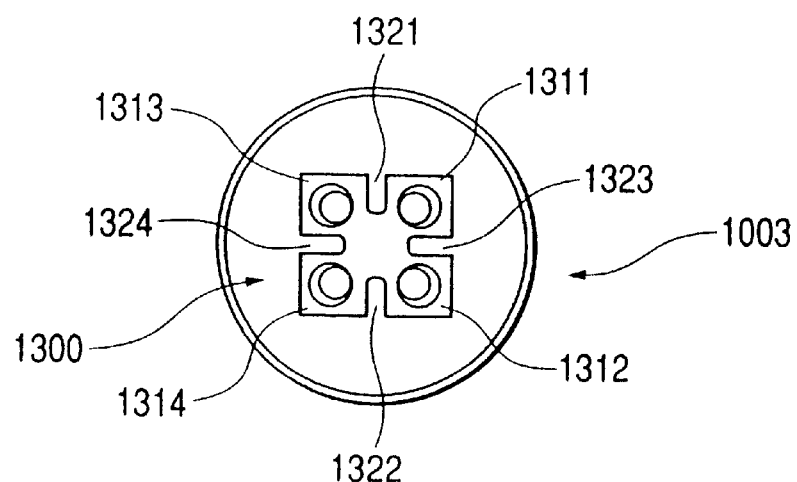
FIG. 32 is a plan view of a front end of an insulator in FIG. 29.

An insulator 1003 is fixedly disposed in a portion of the atmosphere-side cover 1121 which extends near a front end (a lower end) 1128 thereof. The insulator 1003 extends above the housing 1010. The insulator 1003 is spaced from the housing 1010 by a small axial distance. As shown in FIG. 32, the insulator 1003 has four second insertion holes 1311, 1312, 1313, and 1314.

Figure 33:
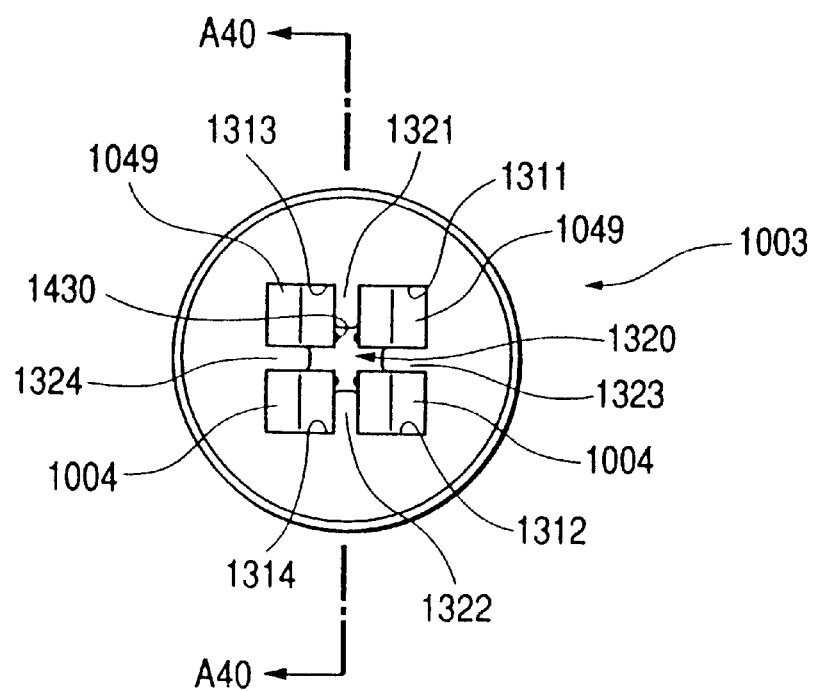
FIG. 33 is a plan view of metal terminals and the front end of the insulator in FIG. 29.
Figure 34:
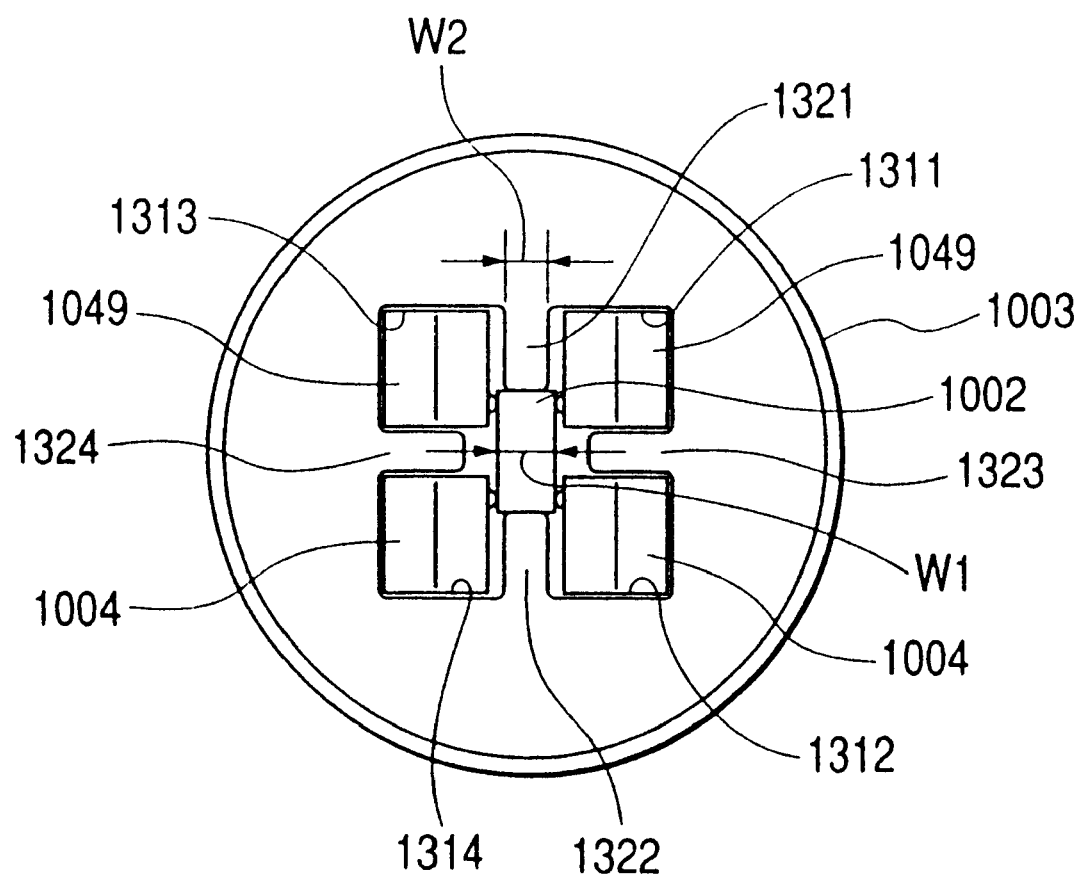
FIG. 34 is a plan view of a sensor element, the metal terminals, and the front end of the insulator in FIG. 29.

As shown in FIG. 29, four leads including leads 1161 and 1163 are placed in the first insertion holes 1511–1514 of the resilient insulator 1005, respectively. As shown in FIGS. 33 and 34, conductor leaf springs (metal terminals) 1004 and 1049 are placed in the second insertion holes 1311–1314 of the insulator 1003, respectively. A shape of the conductor leaf springs 1004 and a shape of the conductor leaf springs 1049 are in a left-right inverted relation. As shown in FIGS. 35 and 36, each of the conductor leaf springs (the metal terminals) 1004 and 1049 has a connecting portion 1041 and a resilient contact portion 1045.

As shown in FIG. 29, the leads including the leads 1161 and 1163 are electrically connected to the conductor leaf springs 1004 and 1049 via metal members including metal members 1151 and 1153.

Figure 37:
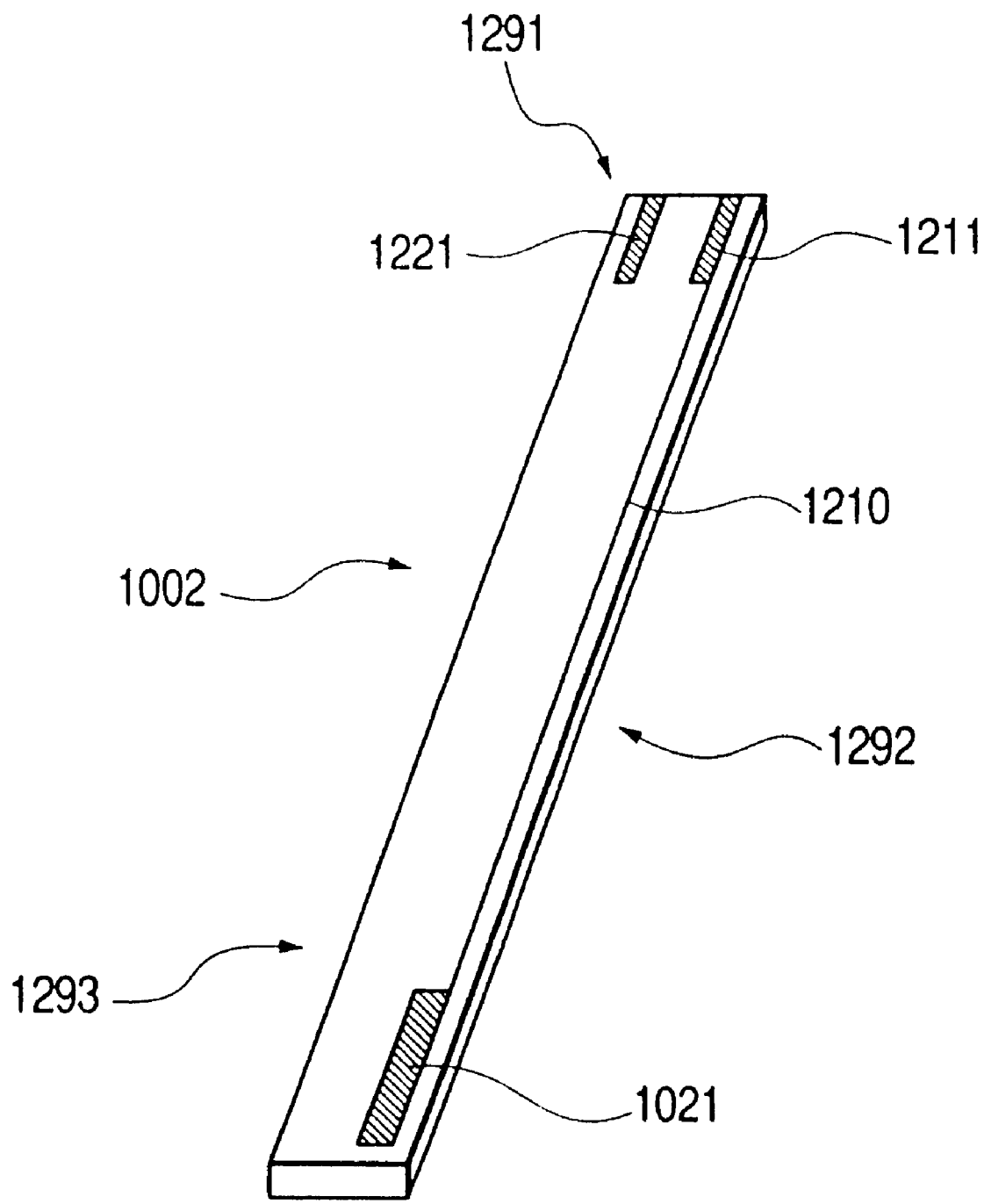
FIG. 37 is a perspective view of the sensor element in FIG. 29.

As shown in FIG. 37, the sensor element 1002 has a base end 1291 provided with four terminal electrodes including terminal electrodes 1211 and 1221. The resilient contact portions 1045 of the conductor leaf springs 1004 and 1049 are in contact with the terminal electrodes on the sensor element 1002, respectively. Thus, the resilient contact portions 1045 of the conductor leaf springs 1004 and 1049 are electrically connected with the terminal electrodes on the sensor element 1002, respectively.

As shown in FIG. 37, the terminal electrodes 1211 and 1221 extend on an upper surface of the sensor element 1002. An output signal of the sensor element 1002 appears between the terminal electrodes 1211 and 1221. The other terminal electrodes extend on a lower surface of the sensor element 1002. The other terminal electrodes are electrically connected to a heater within the sensor element 1002, and are used to feed electric power to the heater.

As shown in FIG. 29, a chamber 1011 is formed in the atmosphere-side cover 1121. The chamber 1011 extends between the resilient insulator 1005 and the insulator 1003. The holes 1123 and 1124 in the atmosphere-side covers 1121 and 1122 face the chamber 1011, and communicate therewith.

As shown in FIGS. 30 and 31, a front end (a lower end) 1500 of the resilient insulator 1005 has first guide portions 1531, 1532, 1533, and 1534 which define front ends (lower ends) of the first insertion holes 1511, 1512, 1513, and 1514 respectively.

Figure 38:
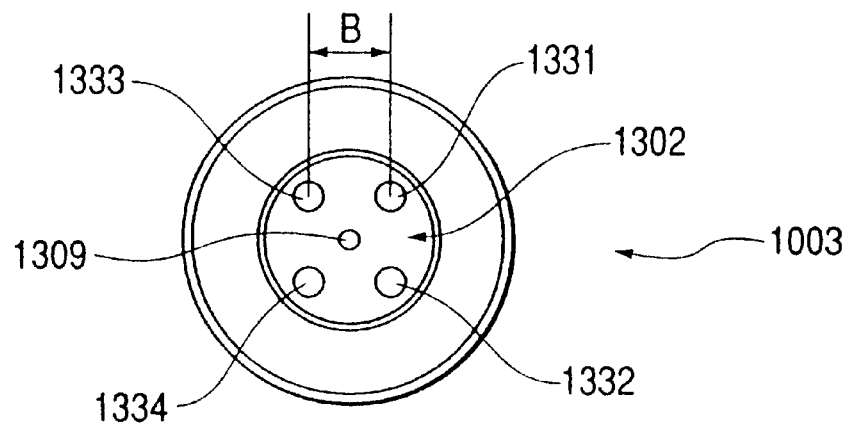
FIG. 38 is a plan view of a base end of the insulator in FIG. 29.
Figure 39:
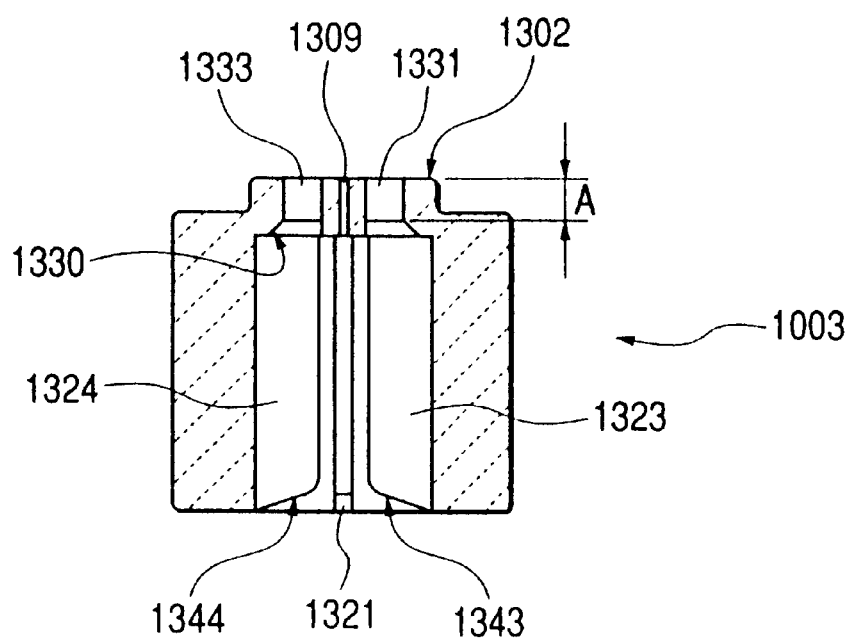
FIG. 39 is a sectional view of the insulator in FIG. 38.

As shown in FIGS. 32, 38, and 39, a base end (an upper end) 1302 of the insulator 1003 has second guide portions 1331, 1332, 1333, and 1334 which define base ends (upper ends) of the second insertion holes 1311, 1312, 1313, and 1314 respectively.

The first guide portions 1531–1534 and the second guide portions 1311–1314 restrict motion of the leads including the leads 1161 and 1163, motion of the metal members including the metal members 1151 and 1153, and motion of the conductor leaf springs (the metal terminals) 1004 and 1049.

The gas sensor 1001 in FIG. 29 will be described below in more detail. The gas sensor 1001 includes the housing 1010, the atmosphere-side covers 1121 and 1122, and measurement-gas-side covers 1141 and 1142. The atmosphere-side cover 1121 is provided on the base end (the upper end) 1101 of the housing 1010. The atmosphere-side cover 1122 is provided on the upper portion of the atmosphere-side cover 1121. The atmosphere-side cover 1122 extends outward of the upper portion of the atmosphere-side cover 1121. The housing 1010 has a front end (a lower end) 1102 on which the measurement-gas-side covers 1141 and 1142 are provided. The measurement-gas-side covers 1141 and 1142 compose a double-wall structure. The measurement-gas-side cover 1142 extends inward of the measurement-gas-side cover 1141.

The sensor element 1002 is inserted into the housing 1010. The sensor element 1002 is fixed with respect to the housing 1010. As shown in FIG. 37, the terminal electrodes 1211 and 1221 are provided on the base end 1291 of the sensor element 1002. The sensor element 1002 has a front end (a lower end) 1293 on which a measurement-gas-side electrode 1021 is provided. The base end 1291 of the sensor element 1002 is located in the insulator 1003 within the atmosphere-side cover 1121. The front end (the lower end) 1293 of the sensor element 1002 is located in the measurement-gas-side cover 1142.

As shown in FIG. 37, the measurement-gas-side electrode 1021 is provided on the front end (the lower end) 1293 of the sensor element 1002. A reference electrode is provided on the sensor element 1002. Specifically, the reference electrode faces an atmosphere chamber formed in the sensor element 1002. A lead portion 1210 formed on the sensor element 1002 electrically connects the measurement-gas-side electrode 1021 and the terminal electrode 1211. Similarly, a lead portion formed on the sensor element 1002 electrically connects the reference electrode and the terminal electrode 1221. An output signal of the sensor element 1002 which appears between the measurement-gas-side electrode 1021 and the reference electrode can be transmitted to an external via the terminal electrodes 1211 and 1221.

A passage formed in the sensor element 1002 extends from the base end 1291 thereof, and leads to the atmosphere chamber therein. The passage in the sensor element 1002 introduces atmosphere into the atmosphere chamber.

With reference to FIG. 37, the two terminal electrodes 1211 and 1221 extend on the upper surface of the sensor element 1002. Two terminal electrodes (not shown) extending on the lower surface of the sensor element 1002 are electrically connected to a heater contained in the sensor element 1002. Electric power can be fed to the heater via the terminal electrodes extending on the lower surface of the sensor element 1002. The heater can be activated by the electric power.

As shown in FIG. 29, the atmosphere-side cover 1121 is welded to the housing 1010. The atmosphere-side cover 1122 is fixed to the upper portion of the atmosphere-side cover 1121 by pressing and deforming processes. A water repellent filter 1125 is provided between the atmosphere-side covers 1121 and 1122. The atmosphere-side covers 1121 and 1122 have the holes 1123 and 1124 in communication with the chamber 1011. The water repellent filter 1125 is interposed between the holes 1123 and 1124.

A lower insulator 1013 having a cylindrical shape is located in the housing 1010. A central portion 1292 (see FIG. 37) of the sensor element 1002 extends through the lower insulator 1013. The central portion 1292 of the sensor element 1002 is fixed to the lower insulator 1013. Glass sealant 1131 and glass sealant 1132 provide sealing between the lower insulator 1013 and the central portion 1292 of the sensor element 1002.

As shown in FIG. 29, the insulator 1003 is located in the atmosphere-side cover 1121. The insulator 1003 extends above the lower insulator 1013. The resilient insulator 1005 is located in an upper end of the atmosphere-side cover 1121. The resilient insulator 1005 extends above the insulator 1003. The resilient insulator 1005 has the four first insertion holes 1511–1514 into which the four leads including the leads 1161 and 1163 are inserted respectively.

The insulator 1003 has the four second insertion holes 1311–1314 in which the conductor leaf springs (the metal terminals) 1004 and 1049 are placed respectively. The four leads including the leads 1161 and 1163 are electrically connected to the conductor leaf springs 1004 and 1049 via the metal members (including the metal members 1151 and 1153), respectively. The metal members (including the metal members 1151 and 1153) are located in the chamber 1011.

As shown in FIGS. 32 and 33, the insulator 1003 has the four second insertion holes 1311–1314. The second insertion holes 1311–1314 are of approximately rectangular or square cross-sections. The second insertion holes 1311–1314 communicate with each other via a space extending at and around the central axis of the insulator 1003.

As shown in FIG. 39, the insulator 1003 has a taper portion 1330 in each of the second insertion holes 1311–1314. Specifically, the taper portion 1330 forms inner surfaces which define a portion of the related second insertion hole 1311, 1312, 1313, or 1314. The insulator 1003 has the second guide portions 1331–1334 which extend above the taper portions 1330. The second guide portions 1331–1334 are of an inside diameter smaller than that of the remainders of the second insertion holes 1311–1314. The second insertion holes 1311–1314 are point-symmetry with respect to the central axis of the insulator 1003. Similarly, the second guide portions 1331–1334 are point-symmetry with respect to the central axis of the insulator 1003.

As shown in FIGS. 32, 33, and 39, the insulator 1003 has ribs 1321, 1322, 1323, and 1324. The ribs 1323 and 1324 are also referred to as the insulating ribs 1323 and 1324. The rib 1321 extends between the second insertion holes 1311 and 1313. The rib 1322 extends between the second insertion holes 1312 and 1314. The rib 1323 extends between the second insertion holes 1311 and 1312. The rib 1324 extends between the second insertion holes 1313 and 1314. The ribs 1321–1324 have bottom surfaces including bottom surfaces 1343 and 1344 located at a lower end 1300 of the insulator 1003. The bottom surfaces of the ribs 1321–1324 taper and extend along inclined directions from the central axis of the insulator 1003 toward the outer circumference thereof.

As shown in FIGS. 38 and 39, an atmosphere introduction hole 1309 extends through a central area of the base end (the upper end) 1302 of the insulator 1003. The second guide portions 1331–1334 of the insulator 1003 have an axial length "A" preferably in the range of 1 mm to 5 mm. More preferably, the axial length "A" is equal to 2 mm. The distance "B" between the centers of adjacent ones of the second guide portions 1331–1334 is preferably in the range of 3 mm to 6 mm. More preferably, the distance "B" is equal to 4.5 mm.

As shown in FIGS. 30 and 31, the resilient insulator 1005 has the four first insertion holes 1511–1514. The first insertion holes 1511–1514 are of a circular cross-section. Inner surfaces of the resilient insulator 1005 which define the first insertion holes 1511–1514 are formed with steps. The first guide portions 1531–1534 extend frontward (downward) from the steps in the first insertion holes 1511–1514, respectively. The first guide portions 1531–1534 are greater in diameter than the portions of the first insertion holes 1511–1514 extending above the steps. As shown in FIG. 30, the original shape of the resilient insulator 1005 is a cylinder. During assembly, the resilient insulator 1005 is fitted into the atmosphere-side covers 1121 and 1122, and is fixed thereto by pressing and deforming them. The axial length "C" (see FIG. 30) of the first guide portions 1531–1534 in the resilient insulator 1005 is preferably in the range of 3 mm to 8 mm. More preferably, the axial length "C" is equal to 5 mm.

Preferably, the distance between the centers of adjacent ones of the second guide portions 1331–1334 in the insulator 1003 is equal or close to the distance between the centers of adjacent ones of the first guide portions 1531–1534 in the resilient insulator 1005. Preferably, lines connecting the leads (including the leads 1161 and 1163), the metal members (including the metal members 1151 and 1153), and the conductor leaf springs (the metal terminals) 1004 and 1049 are straight, and are parallel with the central axis of the body of the gas sensor 1001. In this case, it is possible to more reliably prevent unwanted contact between the leads (including the leads 1161 and 1163), unwanted contact between the metal members (including the metal members 1151 and 1153), and unwanted contact between the conductor leaf springs (the metal terminals) 1004 and 1049.

As shown in FIGS. 35 and 36, each of the metal terminals (the conductor leaf springs) 1004 has a shoulder portion 1040 in addition to the connecting portion 1041 and the resilient contact portion 1045. The shoulder portion 1040 extends between the connecting portion 1041 and the resilient contact portion 1045. The shoulder portion 1040 is formed by a bend at a right angle.

The resilient contact portion 1045 has a back surface 1042, an element contact surface 1043, and a folded portion 1044. The back surface 1042 faces the walls of the insulator 1003 which define the second insertion hole 1311, 1312, 1313, or 1314. The element contact surface 1043 faces the sensor element 1002. The folded portion 1044 extends toward the back surface 1042.

A projection 1430 is provided on the element contact surface 1043. The projection 1430 has slanting surfaces 1431 and 1432 located respectively at lower and upper sides as viewed in FIG. 35. The slope of the slanting surface 1431 is gentler than the slope of the slanting surface 1432.

As shown in FIG. 36, the central line 1410 of the connecting portion 1041 and the central line 1450 of the resilient contact portion 1045 are out of alignment by a distance in a left-right direction. Specifically, the central line 1450 extends rightward of the central line 1410. The projection 1430 extends leftward of the central line 1450 of the resilient contact portion 1045.

As previously mentioned, the shape of the metal terminals (the conductor leaf springs) 1004 and the shape of the metal terminals (the conductor leaf springs) 1049 are in the left-right inverted relation. Therefore, in each of the metal terminals 1049, the central line 1450 of a resilient contact portion 1045 extends leftward of the central line 1410 of a connecting portion 1041. In addition, in each of the metal terminals 1049, a projection 1430 extends rightward of the central line 1450 of the resilient contact portion 1045.

According to the offset relation between the connecting portion 1041 and the resilient contact portion 1045 of each of the metal terminals (the conductor leaf springs) 1004 and 1049 and the off-center placement of the projections 1430 thereof, the interval between adjacent ones of the leads including the leads 1161 and 1163 can be greater than the interval between the electrode terminals 1211 and 1221 on the sensor element 1002. Thus, it is possible to reliably prevent short circuit between the leads including the leads 1161 and 1163.

Figure 40:
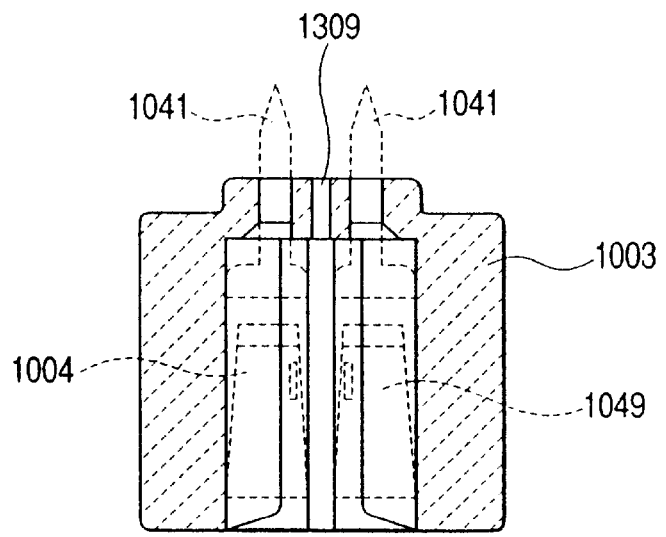
FIG. 40 is a sectional view of the metal terminals and the insulator taken along the lines A40—A40 in FIG. 33.

As best shown in FIGS. 33 and 40, the metal terminal (the conductor leaf spring) 1049 is located in the second insertion hole 1311. The metal terminal (the conductor leaf spring) 1004 is located in the second insertion hole 1312. The metal terminal (the conductor leaf spring) 1049 is located in the second insertion hole 1313. The metal terminal (the conductor leaf spring) 1004 is located in the second insertion hole 1314. The rib 1321 extends between the metal terminals 1049. The rib 1322 extends between the metal terminals 1004. The insulating rib 1323 extends between the metal terminals 1049 and 1004 in the second insertion holes 1311 and 1312. The insulating rib 1324 extends between the metal terminals 1049 and 1004 in the second insertion holes 1313 and 1314.

The metal terminals 1004 and 1049 in the second insertion holes 1311–1314 are in contact with the ribs 1321 and 1322 while being deformed from their original shapes and being contracted in radial directions with respect to the insulator 1003. The insulator 1003 is formed with an element accommodation space 1320 surrounded by the four metal terminals 1004 and 1049, the ribs 1321 and 1322, and the insulating ribs 1323 and 1324.

FIG. 34 shows a condition in which the sensor element 1002 is placed in the element accommodation space 1320 in the insulator 1003. The thickness W2 of the ribs 1321 and 1322 is smaller than the thickness W1 of the sensor element 1002. Therefore, before the sensor element 1002 is placed in position, a thickness of the gap between the metal terminals 1004 and 1049 is smaller than the thickness W1 of the sensor element 1002. Before the sensor element 1002 is placed in position, the resilient contact portions 1045 of the metal terminals 1004 and 1049 in the second insertion holes 1311–1314 are in contact with the ribs 1321 and 1322 while being deformed from their original shapes and being contracted in radial directions with respect to the insulator 1003. As the sensor element 1002 is inserted into the element accommodation space 1320, the sensor element 1002 meets the resilient contact portions 1045 of the metal terminals 1004 and 1049. Then, the sensor element 1002 forces the resilient contact portions 1045 away from each other. In other words, the resilient contact portions 1045 are resiliently deformed by the sensor element 1002. The resilient deformations of the resilient contact portions 1045 cause restoring forces which provide reliable mechanical and electrical contact between the sensor element 1002 and the metal terminals 1004 and 1049. The projections 1430 on the resilient contact portions 1045 of the metal terminals 1004 and 1049 make more reliable the electric contact between the metal terminals 1004 and 1049 and the terminal electrodes on the sensor element 1002. It should be noted that the projections 1430 may be provided on the terminal electrodes of the sensor element 1002 rather than the resilient contact portions 1045 of the metal terminals 1004 and 1049.

With reference to FIG. 29, atmosphere flows into the chamber 1011 in the body of the gas sensor 1001 via the holes 1123 in the atmosphere-side cover 1122, the water repellent filter 1125, and the holes 1124 in the atmosphere-side cover 1121. Atmosphere flows from the chamber 1011 to a region within the insulator 1003 near the second insertion holes 1311–1314 via the atmosphere introduction hole 1309 in the insulator 1003 and the spaces between the metal terminals 1004 and 1049 and the inner surfaces of the insulator 1003 in the second guide portions 1331–1334. The passage in the sensor element 1002 which leads to the atmosphere chamber therein is open at the sensor-element base end 1291 located in the region near the second insertion holes 1311–1314. Atmosphere flows from the region near the second insertion holes 1311–1314 to the atmosphere chamber in the sensor element 1002 via the passage therein.

Since the holes 1123 and 1124 in the atmosphere-side covers 1121 and 1122 face the chamber 1011, atmosphere can be smoothly introduced into the chamber 1011 via the holes 1123 and 1124. Thus, atmosphere can be supplied into the atmosphere chamber in the sensor element 1002 at a sufficient rate.

The first guide portions 1531–1534 and the second guide portions 1311–1314 restrict motion of the leads including the leads 1161 and 1163, motion of the metal members including the metal members 1151 and 1153, and motion of the metal terminals (the conductor leaf springs) 1004 and 1049. Thus, during assembly, it is possible to prevent short circuit between the leads including the leads 1161 and 1163, short circuit between the metal members including the metal members 1151 and 1153, and short circuit between the metal terminals (the conductor leaf springs) 1004 and 1049. The first guide portions 1531–1534 and the second guide portions 1311–1314 make the gas sensor 1001 vibration-resistant.

As shown in FIGS. 35 and 36, the metal terminals (the conductor leaf springs) 1004 and 1049 have plate-like shapes. Thus, the metal terminals 1004 and 1049 hardly rotate in the second insertion holes 1311–1314. Accordingly, during assembly, it is possible to prevent unwanted rotation of the metal terminals 1004 and 1049 which might cause short circuit therebetween.

In the gas sensor 1001, the base end (the upper end) 1291 of the sensor element 1002 is located in the element accommodation space 1320 extending between the metal terminals 1004 and 1049 and the ribs 1321 and 1322. Before the sensor element 1002 is place in position, the resilient contact portions 1045 of the metal terminals 1004 and 1049 are in contact with the ribs 1321 and 1322 while being resiliently deformed from their original shapes and being contracted in radial direction with respect to the insulator 1003. Thus, even before the sensor element 1002 is placed in position, a gap is formed between the resilient contact portions 1045 of the metal terminals 1004 and 1049 by the ribs 1321 and 1322. As the sensor element 1002 is inserted into the element accommodation space 1320, the sensor element 1002 meets the resilient contact portions 1045 of the metal terminals 1004 and 1049. Then, the sensor element 1002 forces the resilient contact portions 1045 away from each other, and expands the gap therebetween by only a small degree. Accordingly, the sensor element 1002 receives only weak forces from the resilient contact portions 1045 of the metal terminals 1004 and 1049. Thus, the sensor element 1002 is prevented from being damaged. In addition, the sensor element 1002 can easily be placed in position.

Before the sensor element 1002 is placed in position, the resilient contact portions 1045 of the metal terminals 1004 and 1049 are in contact with the ribs 1321 and 1322 while being resiliently deformed from their original shapes and being contracted in the radial directions. Accordingly, the effective width of the metal terminals 1004 and 1049, which occur when they are inserted into the second insertion holes 1311–1314, can be smaller. Thus, even in the case where the second insertion holes 1311–1314 are narrow, it is possible to surely form the element accommodation space 1320 between the metal electrodes 1004 and 1049 and the ribs 1321 and 1322.

The thickness W2 of the ribs 1321 and 1322 is smaller than the thickness W1 of the sensor element 1002. Therefore, before the sensor element 1002 is placed in position, a thickness of the gap between the metal terminals 1004 and 1049 is smaller than the thickness W1 of the sensor element 1002. Before the sensor element 1002 is placed in position, the resilient contact portions 1045 of the metal terminals 1004 and 1049 are in contact with the ribs 1321 and 1322. As the sensor element 1002 is inserted into the element accommodation space 1320, the sensor element 1002 meets the resilient contact portions 1045 of the metal terminals 1004 and 1049. Then, the sensor element 1002 forces the resilient contact portions 1045 away from each other while contracting the metal terminals 1004 and 1049 in the radial directions of the insulator 1003. In other words, the resilient contact portions 1045 are resiliently deformed by the sensor element 1002. The resilient deformations of the resilient contact portions 1045 cause restoring forces which provide reliable mechanical and electrical contact between the sensor element 1002 and the metal terminals 1004 and 1049.

During assembly, the metal terminals 1004 and 1049 are placed into the second insertion holes 1311–1314 while being deformed and contracted from their original shapes. In this case, the metal terminals 1004 and 1049 can be prevented from interfering with each other. Thus, the metal terminals 1004 and 1049 can easily be placed into the second insertion holes 1311–1314.

The projections 1430 are provided on the resilient contact portions 1045 of the metal terminals 1004 and 1049. The projections 1430 provide more reliable electric contact between the metal terminals 1004 and 1049 and the terminal electrodes including the terminal electrodes 211 and 221 on the sensor element 1002.

As shown in FIG. 35, the projection 1430 has the slanting surfaces 1431 and 1432. The slanting surface 1431 faces a direction along which the sensor element 1002 is moved during its placement in position. Thus, the sensor element 1002 relatively slides on the slanting surface 1431 during its placement in position. The slope of the slanting surface 1431 is gentler than the slope of the slanting surface 1432. Accordingly, it is possible to easily place the sensor element 1002 in position.

The rib 1323 of the insulator 1003 provides reliable insulation between the metal terminals 1004 and 1049. Also, the rib 1324 of the insulator 1003 provides reliable insulation between the metal terminals 1004 and 1049.

In each of the metal terminals 1004 and 1049, the shoulder 1040 which extends between the connecting portion 1041 and the resilient contact portion 1045 is formed by a bend at a right angle. Thus, it is easy to carry the metal terminals 1004 and 1049. Each of the metal terminals 1004 and 1049 can be shorter than the prior-art metal terminal 94 in FIG. 2 which lacks a right-angled shoulder portion. Therefore, it is possible to miniaturize the gas sensor 1001.

As shown in FIG. 36, the central line 1410 of the connecting portion 1041 and the central line 1450 of the resilient contact portion 1045 in each of the metal terminals 1004 and 1049 are out of alignment. Thus, as shown in FIG. 40, the connecting portions 1041 of the metal terminals 1004 and 1049 can be closer to the central axis of the insulator 1003. Accordingly, it is possible to miniaturize the insulator 1003.

Twelfth Embodiment

A twelfth embodiment of this invention is similar to the eleventh embodiment thereof except that a sensor element 1002A replaces the sensor element 1002.

Figure 41:
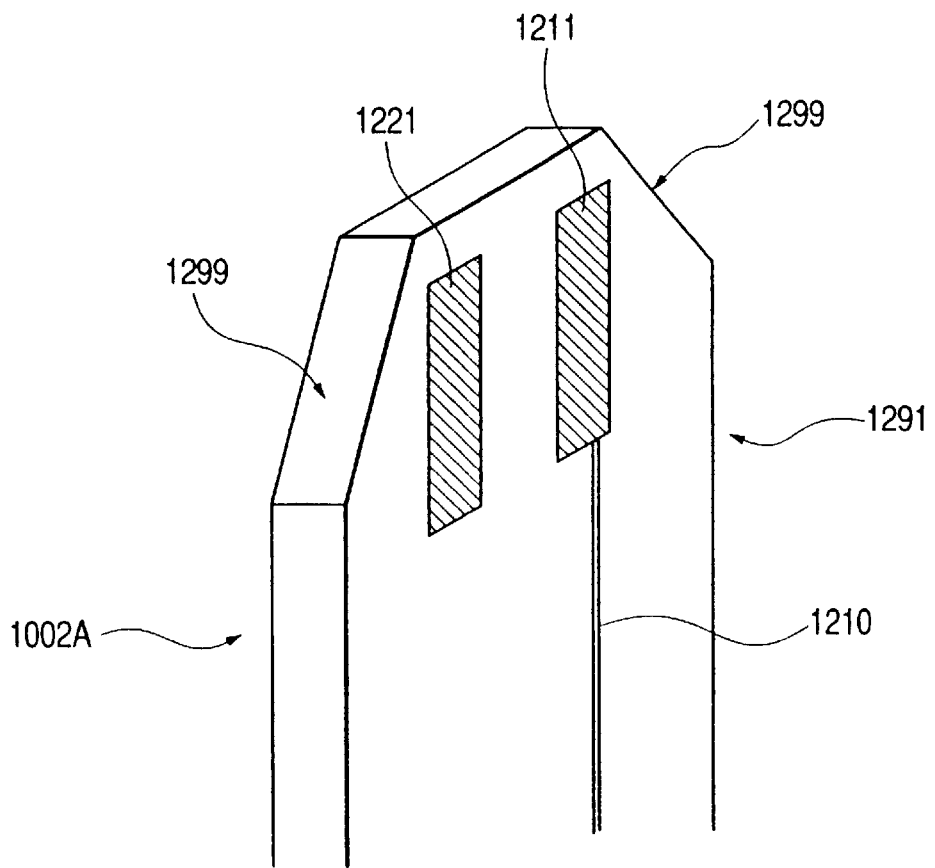
FIG. 41 is a perspective view of a base end of a sensor element in a gas sensor according to a twelfth embodiment of this invention.

As shown in FIG. 41, the sensor element 1002A has a base end (an upper end) 1291 formed with taper portions 1299. The taper portions 1299 enable the sensor element 1002A to be smoothly placed into the element accommodation space 1320 (see FIG. 33).

Thirteenth Embodiment

Figure 42:
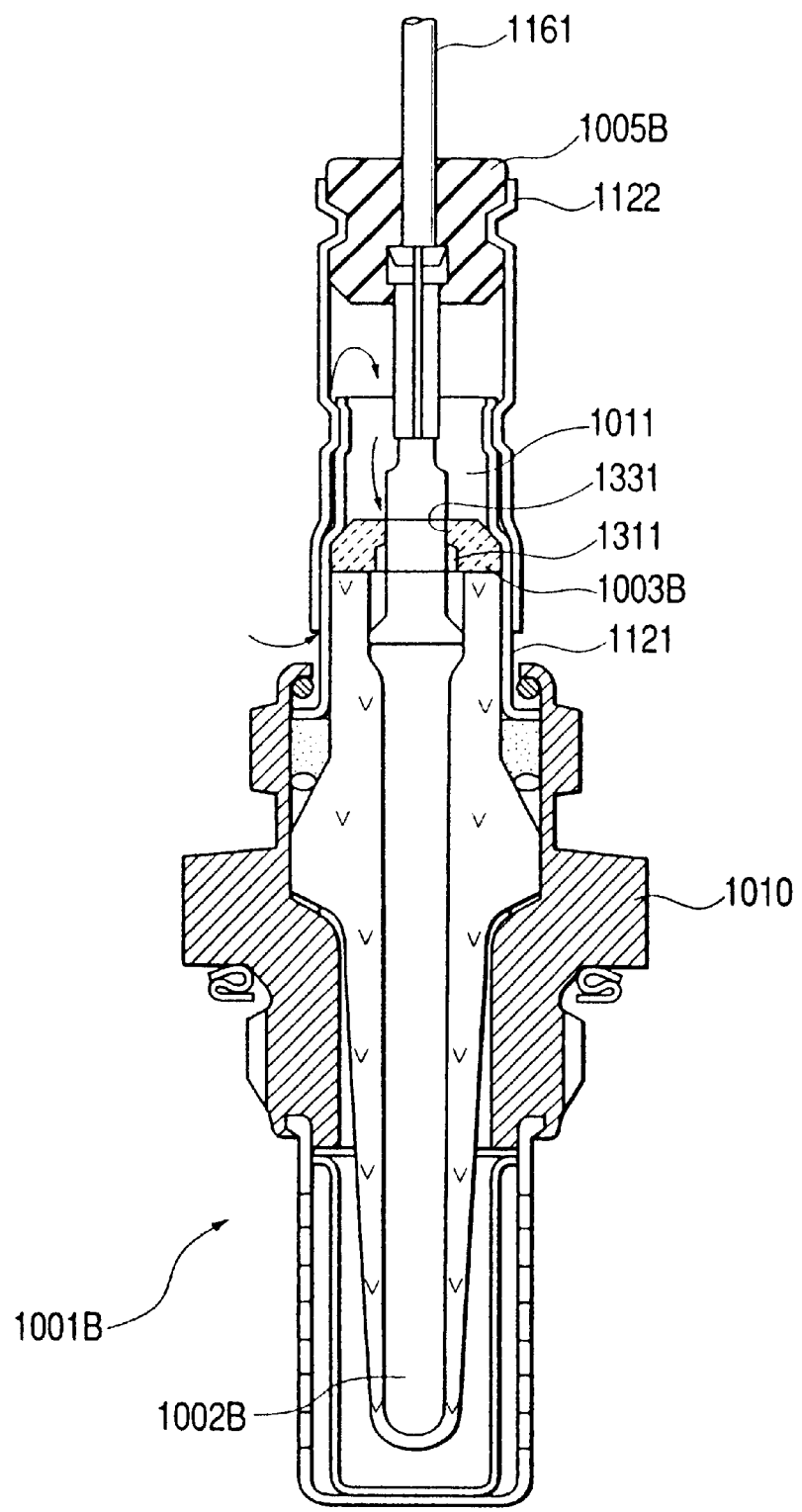
FIG. 42 is a sectional view of a gas sensor according to a thirteenth embodiment of this invention.

FIG. 42 shows a gas sensor 1001B according to a thirteenth embodiment of this invention. The gas sensor 1001B in FIG. 42 is similar to the gas sensor 1001 in FIG. 29 except for design changes mentioned hereinafter.

The gas sensor 1001B in FIG. 42 contains a cup-shaped sensor element 1002B. The sensor element 1002B is inserted into a housing 1010. The sensor element 1002B is fixed with respect to the housing 1010.

An atmosphere-side cover 1121 is provided on a base end (an upper end) of the sensor element 1002B. An atmosphere-side cover 1122 is provided on a base end (an upper end) of the atmosphere-side cover 1121. The atmosphere-side covers 1121 and 1122 are fixed to each other by pressing and deforming them at eight points. Atmosphere flows from an external into a chamber 1011 within the body of the gas sensor 1001B via gaps between the atmosphere-side covers 1121 and 1122 at the pressing and deforming points.

A front end (a lower end) of the sensor element 1002B has a measurement-gas-side electrode and a reference electrode. The base end (an upper end) of the sensor element 1002B has a terminal electrode which is electrically connected with the reference electrode. In addition, the terminal electrode on the sensor element 1002B is electrically connected with a lead 1161 extending through a resilient insulator 1005B. The resilient insulator 1005B fits into a base end (an upper end) of the atmosphere-side cover 1122. The measurement-gas-side electrode on the sensor element 1002B is electrically connected with the housing 1010 via a floating packing. An output signal of the sensor element 1002B is transmitted to an external device via the lead 1161 and the housing 1010.

The gas sensor 1001B in FIG. 42 contains an insulator 1003B. The insulator 1003B has a second insertion hole 1311 and a second guide portion 1331. The second guide portion 1331 defines a base end (an upper end) of the second insertion hole 1311. Atmosphere flows from the chamber 1011 toward the reference electrode on the sensor element 1001B via the second guide portion 1331 and the second insertion hole 1311.

Fourteenth Embodiment

Figure 43:
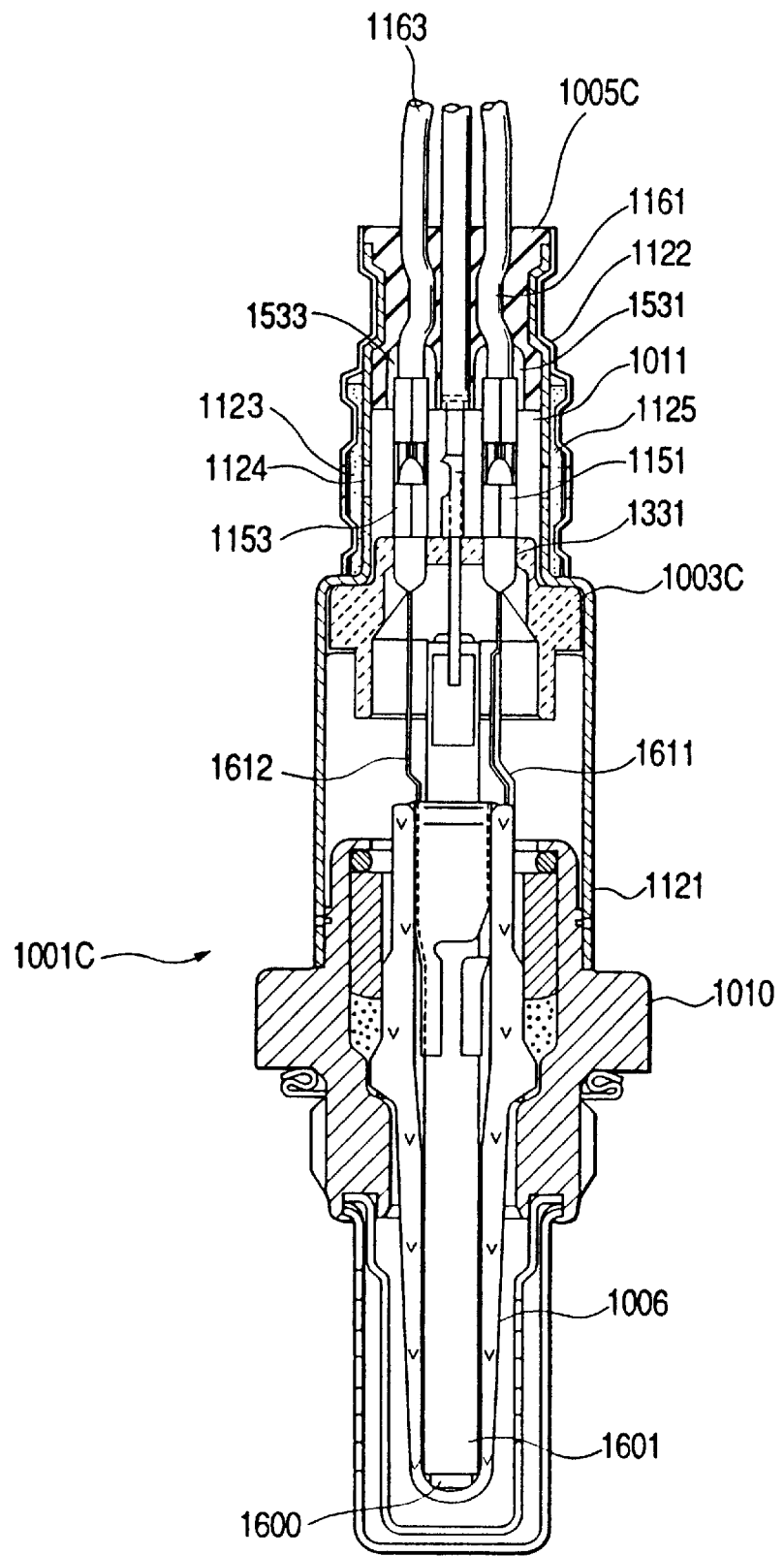
FIG. 43 is a sectional view of a gas sensor according to a fourteenth embodiment of this invention.

FIG. 43 shows a gas sensor 1001C according to a fourteenth embodiment of this invention. The gas sensor 1001C in FIG. 43 is similar to the gas sensor 1001 in FIG. 29 except for design changes mentioned hereinafter.

The gas sensor 1001C in FIG. 43 includes a cup-shaped sensor element 1006. An atmosphere chamber 1600 is formed in the sensor element 1006. The sensor element 1006 includes a bar-like heater 1601 inserted into the atmosphere chamber 1600. The sensor element 1006 is inserted into a housing 1010. The sensor element 1006 is fixed with respect to the housing 1010.

An atmosphere-side cover 1121 is provided on a base end (an upper end) of the housing 1010. An atmosphere-side cover 1122 is provided on an upper portion of the atmosphere-side cover 1121. The atmosphere-side covers 1121 and 1122 are fixed to each other by pressing and deforming them. A water repellent filter 1125 is provided between the atmosphere-side covers 1121 and 1122. The atmosphere-side covers 1121 and 1122 have holes 1123 and 1124.

A resilient insulator 1005C fits into a base end (an upper end) of the atmosphere-side cover 1121. The resilient insulator 1005C has four first insertion holes into which leads including leads 1161 and 1163 are inserted respectively. Thus, the first insertion holes are occupied and blocked by the leads. The resilient insulator 1005C has four first guide portions including first guide portions 1531 and 1533. The first guide portions define front ends (lower ends) of the first insertion holes.

An insulator 1003C is disposed in an intermediate portion of the atmosphere-side cover 1121. The insulator 1003C has four second insertion holes. The insulator 1003 has four second guide portions including second guide portions 1331 and 1333. The second guide portions define base ends (upper ends) of the second insertion holes.

A chamber 1011 is formed in the atmosphere-side cover 1121. The chamber 1011 extends between the resilient insulator 1005C and the insulator 1003C. The holes 1123 and 1124 in the atmosphere-side covers 1121 and 1122 face the chamber 1011. Atmosphere flows from an external into the chamber 1011 via the holes 1123 and 1124 and the water repellent filter 1125. Atmosphere flows from the chamber 1011 toward the atmosphere chamber 1600 via the second guide portions and the second insertion holes in the insulator 1003C.

Metal terminals 1611 and 1612 have resilient contact portions which are electrically connected with terminal electrodes on a base end (an upper end) of the sensor element 1006. Also, the metal terminals 1611 and 1612 are electrically connected with the leads (including the leads 1161 and 1163) via metal members including metal members 1151 and 1153. The sensor element 1006 has an approximately circular cross-section. The metal terminals 1611 fit into outer portions of the sensor element 1006. The metal portions 1612 fit into inner portions of the sensor element 1006. The metal terminals 1612 act as holders for fixedly locating the heater 1601 in the atmosphere chamber 1600.

Fifteenth Embodiment

Figure 44:
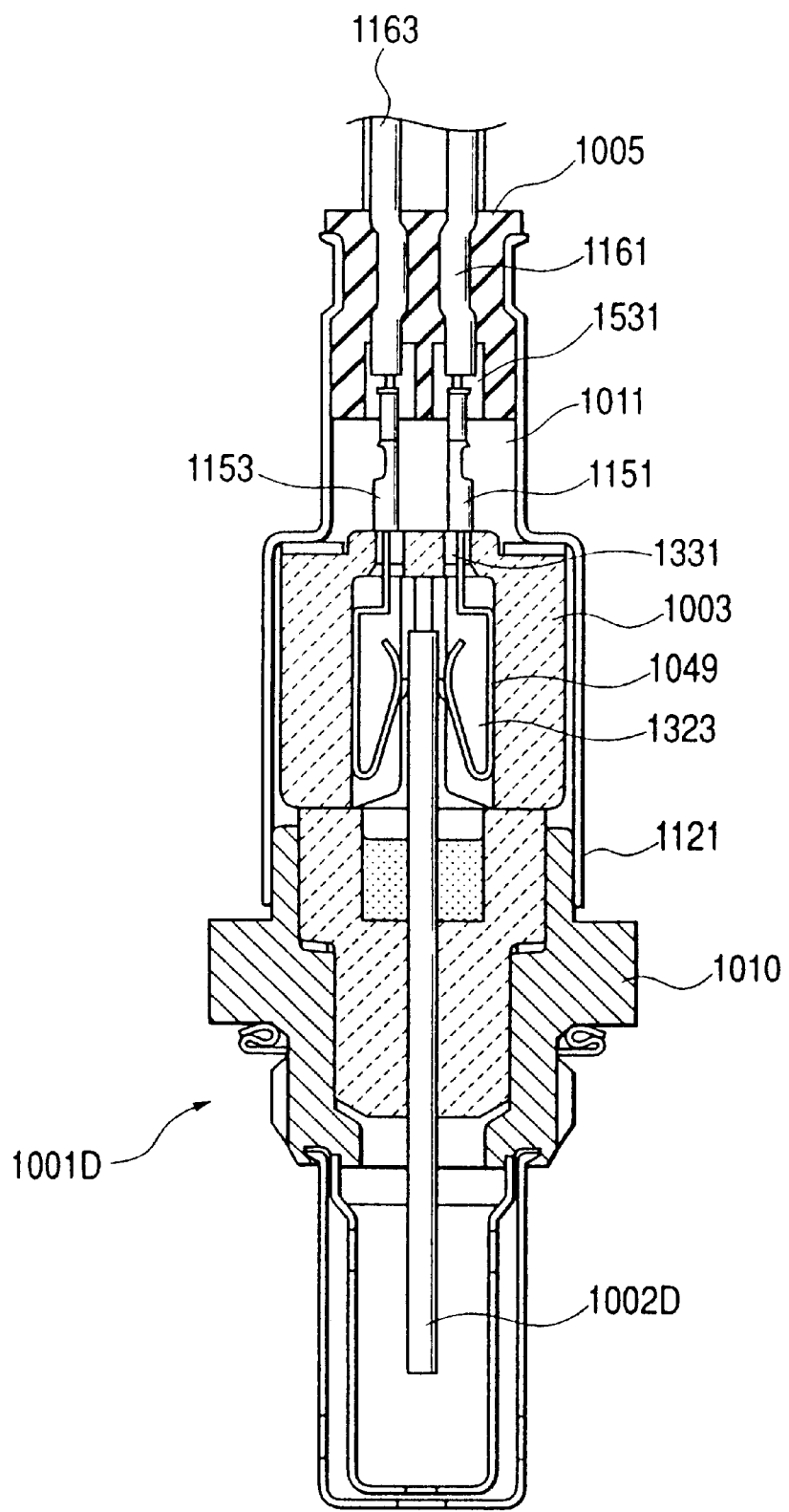
FIG. 44 is a sectional view of a gas sensor according to a fifteenth embodiment of this invention.

FIG. 44 shows a gas sensor 1001D according to a fifteenth embodiment of this invention. The gas sensor 1001D in FIG. 44 is similar to the gas sensor 1001 in FIG. 29 except for design changes mentioned hereinafter.

In the gas sensor 1001D of FIG. 44, the atmosphere-side cover 1122 (see FIG. 29) is omitted, and the atmosphere-side cover 1121 does not have any holes for introducing atmosphere.

The gas sensor 1001D includes a sensor element 1002D provided with a sensor cell and a pumping cell. Drive currents are fed to the sensor cell and the pumping cell, respectively. In general, the direction of the drive current for the pumping cell is opposite to the direction of the drive current for the sensor cell. The pumping cell generates oxygen, and the generated oxygen is supplied to a reference-gas chamber in the sensor element 1002D. The supply of oxygen to the reference-gas chamber enables the oxygen concentration in a measurement gas to be detected. Accordingly, it is unnecessary to supply atmosphere to the reference-gas chamber from an external.

Leads including leads 1161 and 1163 extend into the body of the gas sensor 1001D. Specifically, the leads include leads for electrical connection with the sensor cell, leads for electrical connection with the pumping cell, and leads for electrical connection with a heater in the sensor element 1002D.

What is claimed is:

1. A gas sensor comprising:
   a housing having a base end;
   a sensor element inserted into the housing and fixed with respect to the housing, the sensor element having a base end;
   at least one terminal electrode provided on the base end of the sensor element;

an atmosphere-side cover provided on the base end of the housing and having a base end and a front end;

a resilient insulating member provided on the base end of the atmosphere-side cover, and having at least one first insertion hole;

an insulator provided in the front end of the atmosphere-side cover and having at least one second insertion hole;

a lead placed in the first insertion hole;

a metal terminal placed in the second insertion hole and having a connecting portion electrically connected with the lead and a resilient contact portion electrically connected with the terminal electrode on the base end of the sensor element; and a metal member electrically connecting the metal terminal and the lead;

wherein the resilient insulating member includes a first guide portion defining a front end of the first insertion hole and restricting motion of the lead, and the insulator includes a second guide portion defining a base end of the second insertion hole and restricting motion of the metal terminal, and wherein the first guide portion restricts motion of the metal member.

2. A gas sensor as recited in claim 1, wherein the metal terminal includes a leaf spring.

3. A gas sensor as recited in claim 1, wherein the second guide portion has a length in a range of 1 mm to 5 mm.

4. A gas sensor as recited in claim 1, wherein there are provided a plurality of the second guide portions, and a distance between centers of the second guide portions is in a range of 3 mm to 6 mm.

5. A gas sensor as recited in claim 1, wherein the first guide portion has a length in a range of 3 mm to 8 mm.

6. A gas sensor as recited in claim 1, wherein the metal terminal has a projection in contact with the terminal electrode on the base end of the sensor element.

7. A gas sensor as recited in claim 1, wherein the metal terminal has a shoulder between the connecting portion and the resilient contact portion, the shoulder including a bend at a right angle.

8. A gas sensor as recited in claim 1, wherein a central line of the connecting portion of the metal terminal and a central line of the resilient contact portion thereof are out of alignment.

9. A gas sensor as recited in claim 1, wherein the metal member is inserted into the first guide portion.

10. A gas sensor as recited in claim 1, wherein the atmosphere-side cover contains an internal space located between the resilient insulating member and the insulator, and the atmosphere-side cover has a hole communicating with the internal space for introducing atmosphere into the internal space.

11. A gas sensor as recited in claim 1, wherein the insulator has an atmosphere Introduction passage.

12. A gas sensor as recited in claim 1, wherein the first guide portion comprises a hole into which the metal member extends.

13. A gas sensor comprising:

a housing having a base end;

a sensor element inserted into the housing and fixed with respect to the housing, the sensor element having a base end;

at least one terminal electrode provided on the base end of the sensor element;

an atmosphere-side cover provided on the base end of the housing and having a base end and a front end;

a resilient insulating member provided on the base end of the atmosphere-side cover, and having at least one first insertion hole;

an insulator provided in the front end of the atmosphere-side cover and having at least one second insertion hole;

a lead placed in the first insertion hole; and a metal terminal placed in the second insertion hole and having a connecting portion electrically connected with the lead and a resilient contact portion electrically connected with the terminal electrode on the base end of the sensor element;

wherein the resilient insulating member includes a first guide portion defining a front end of the first insertion hole and restricting motion of the lead, and the insulator includes a second guide portion defining a base end of the second insertion hole and restricting motion of the metal terminal, wherein the insulator has at least one rib adjacent to the second insertion hole, the rib having a thickness smaller than a thickness of the sensor element, the metal terminal being in contact with the rib while being contracted in a radial direction of the insulator, and wherein the base end of the sensor element is placed in an element accommodation space formed between the rib and the metal terminal.

14. A gas sensor as recited in claim 13, wherein there are provided a plurality of the ribs and a plurality of the metal terminals, the ribs including ribs for locating the metal terminals and ribs for electrically insulating the metal terminals from each other.

* * * * *